(12) United States Patent
Noda et al.

(10) Patent No.: US 9,683,942 B2
(45) Date of Patent: Jun. 20, 2017

(54) LUMINESCENCE MEASURING DEVICE

(71) Applicant: Hitachi High-Technologies Corporation, Minato-ku, Tokyo (JP)

(72) Inventors: Hideyuki Noda, Tokyo (JP); Masahiro Okanojo, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 135 days.

(21) Appl. No.: 14/411,271

(22) PCT Filed: May 22, 2013

(86) PCT No.: PCT/JP2013/064267
§ 371 (c)(1),
(2) Date: Dec. 24, 2014

(87) PCT Pub. No.: WO2014/002653
PCT Pub. Date: Jan. 3, 2014

(65) Prior Publication Data
US 2015/0253250 A1    Sep. 10, 2015

(30) Foreign Application Priority Data
Jun. 27, 2012  (JP) ................................. 2012-143686

(51) Int. Cl.
*G01N 21/76* (2006.01)
*C12M 1/34* (2006.01)
(Continued)

(52) U.S. Cl.
CPC .............. *G01N 21/76* (2013.01); *C12M 1/34* (2013.01); *G01J 1/0252* (2013.01);
(Continued)

(58) Field of Classification Search
CPC ........ C12M 1/34; G01J 1/0252; G01N 21/76; G01N 2201/1211; G02B 7/008; H01L 31/024
(Continued)

(56) References Cited

U.S. PATENT DOCUMENTS 3,998,592 A    12/1976   Pyle
7,879,290 B2   2/2011    Noda et al.
(Continued)

FOREIGN PATENT DOCUMENTS

JP    8-285777 A    11/1996
JP    2711679 B2    2/1998
(Continued)

OTHER PUBLICATIONS

International Search Report dated Jun. 18, 2013 with English translation (seven (7) pages).

*Primary Examiner* — Michael Hobbs
(74) *Attorney, Agent, or Firm* — Crowell & Moring LLP

(57) ABSTRACT

The present invention relates to a luminescence measuring device that includes a holder that holds a container for containing a sample, a plate member that holds the holder, a light detector that detects luminescence in the sample, and has a light receiving surface facing a bottom surface of the container, a first temperature control unit that performs control of a temperature of the light detector, and a ventilator that sends air to the light receiving surface of the light detector. The first temperature control unit may be provided on a side face of the light detector, and provided with a flow path therein. The air sending may be performed via the flow path in the first temperature control unit, so that the air having the same temperature as that of the light detector is sent to the light receiving surface.

15 Claims, 20 Drawing Sheets

(51) Int. Cl.
*G01J 1/02* (2006.01)
*G02B 7/00* (2006.01)
*H01L 31/024* (2014.01)

(52) U.S. Cl.
CPC .............. *G01N 2201/0231* (2013.01); *G01N 2201/1211* (2013.01); *G02B 7/008* (2013.01); *H01L 31/024* (2013.01)

(58) Field of Classification Search
USPC ..................................................... 435/288.7
See application file for complete search history.

(56) References Cited

U.S. PATENT DOCUMENTS

| | | | |
|---|---|---|---|
| 2006/0092506 A1* | 5/2006 | Tsuchiya | G02B 7/008 359/395 |
| 2006/0121602 A1* | 6/2006 | Hoshizaki | G01N 21/645 435/288.7 |
| 2011/0032614 A1 | 2/2011 | Liedtke et al. | |
| 2012/0149050 A1* | 6/2012 | Lapen | G01N 35/00029 435/29 |

FOREIGN PATENT DOCUMENTS

| | | |
|---|---|---|
| JP | 11-142242 A | 5/1999 |
| JP | 2008-268019 A | 11/2008 |
| JP | 2010-216839 A | 9/2010 |

* cited by examiner

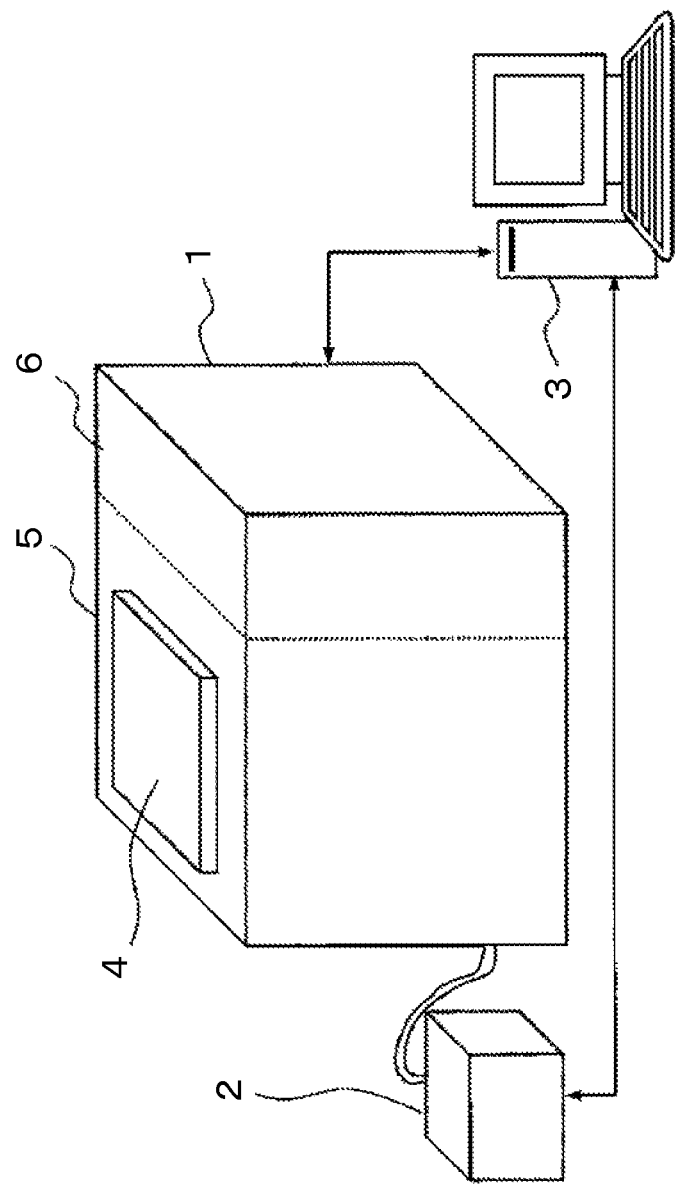

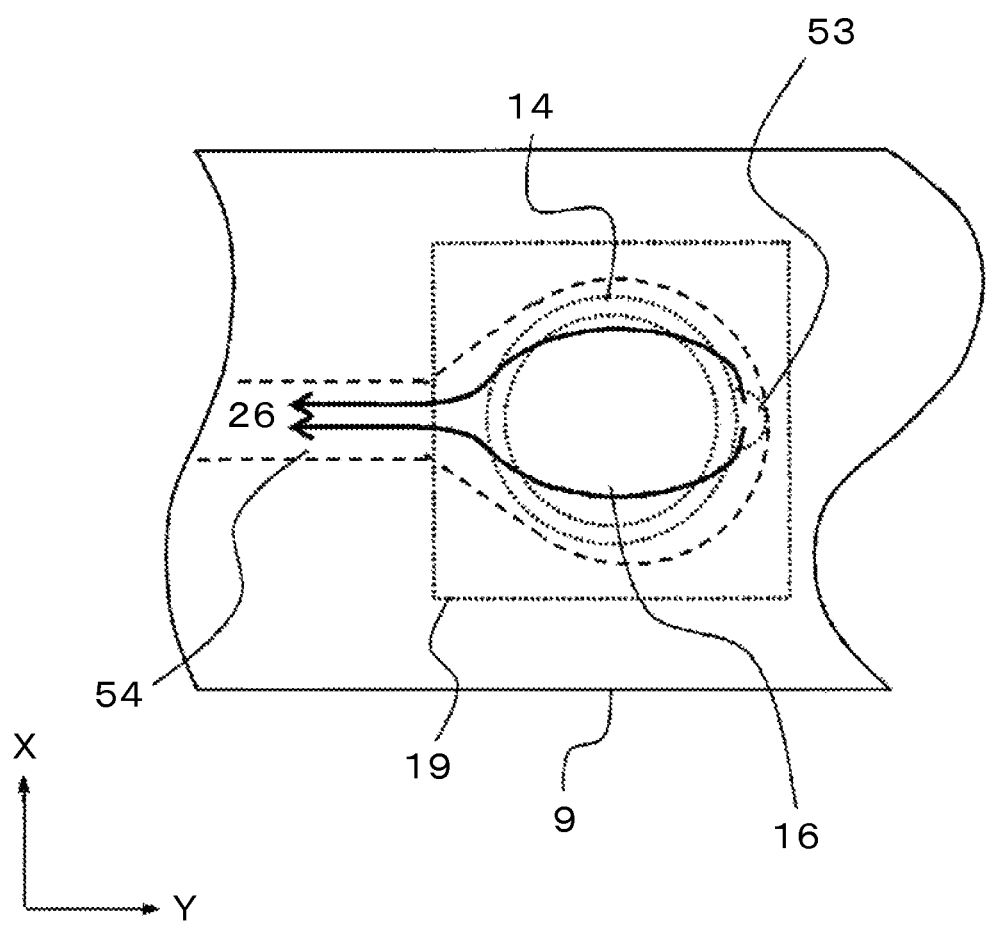

NOT TEMPERATURE-ADJUSTED

TEMPERATURE-ADJUSTED TO 20° C

LUMINESCENCE MEASURING DEVICE

TECHNICAL FIELD

The present invention relates to luminescence detection with respect to a substance contained in a sample. In particular, it relates to a weak luminescence detection device adapted to detect chemiluminescence and bioluminescence of the substance contained in the sample with high sensitivity and high precision.

BACKGROUND ART

There is a contamination control standard for a biocleanroom indoor environment that has been provided under the pharmacopeia for pharmaceutical manufacturing facilities and it is required to maintain to be less than one bacterium (CFU: Colony-Forming Unit) in a safety cabinet and to be less than 10 CFU in an neighborhood area thereof per 1 $m^3$ of air. Here, CFU is a unit that indicates the number of living bacteria (viable bacteria). In addition, there is also a contamination control standard that has been provided under the pharmacopeia for sterile water (water for use in pharmaceuticals) in the pharmaceutical manufacturing facilities, it is required to operate to be less than 10 CFU/100 mL in level water for injection, and a culture method is used for examinations.

However, in the culture method, since a nutrient agar is cultured for 2-3 days or 10 or more days depending on the kind of a bacterial cell used in an incubator and the number of generated colonies is visually counted, the time is taken until a result is obtained. Under such a background, it is desired to develop a rapid measurement method for a contamination monitor and there are a method of detecting metabolism activity when the viable bacteria grow, a method of detecting it as light by utilizing substances in the bacterial cell and so forth.

Since an Adenosine triphosphate (ATP) bioluminescence method (ATP method) of optically detecting it by utilizing the substances in the bacterial cell requires no culturing process, the result is obtained in one hour even when the time taken for sample preparation is included. If it becomes possible to grasp a microbial contamination condition in one hour, check of a line and products (including intermediates) and measures taken for them will be promoted also during work shift for manufacture and it is expected that a safety management system and a shipment system will be remarkably improved.

In the ATP method, the number of ATPs in a cell is measured by converting it into an amount of light by utilizing a luminescent reaction of fireflies. A principle thereof is such that a luciferase enzyme is made to capture substrate luciferin and ATP molecules and an amount of luminescence when luciferin (oxyluciferin that has been oxidized with consumption of the ATPs shifts from an excited state to a ground state is measured.

At this time, since consumption of one ATP molecule is equivalent to generation of one photon, the number of generated photons is proportional to the number of ATPs. Since the ATP molecules equivalent to 1 attomole (amol=$10^{-18}$ mol) are present in the viable bacteria as an energy source, the total number of the viable bacteria contained in a measurement sample can be estimated. Further, because of its quantum efficiency ($\Phi_{SL}$: ≠0.5) that is the most excellent in bioluminescence and chemiluminescence, one cell can be detected as the photons equivalent to hundreds of thousands of ones and thus it is the method capable of detecting light equivalent to one cell by the luminescent reaction in principle.

However, it is reported that a detection lower limit of the ATP method is generally about $10^2$ amol (amol=$10^{-18}$ mol) due to fluctuations in data depending on the performance of a measuring device used and influenced by mixing of the ATP and the bacterial cell present in the environment. As a method of preventing these fluctuations in data, there have been recently reported a dispensing system that possesses a cleaning function for preventing external contamination and a bioluminescence detection system that a highly sensitive light detector has been installed in a space that is light shielded and suppressed in contaminant from the outside in the same device as disclosed, for example, in Patent Literature 1 and it becomes possible to measure the amount of the ATP molecules equivalent to 1 amol.

In addition, in order to improve the performance of the measuring device, there is adopted a means for reducing random noise components and the number of dark pulse counts so as to suppress fluctuations in signal component and extracting the signal component of weak light with high reliability so as to improve detection sensitivity and, for example, in Patent Literature 2, there is disclosed a method of performing temperature control by covering the light detector with a cooling device.

CITATION LIST

Patent Literature

PTL 1: Japanese Patent Application Laid-Open No. 2008-268019

PTL 2: Japanese Patent Application Laid-Open No. H11-142242

SUMMARY OF INVENTION

Technical Problem

In detection of weak light, in order to reduce the dark current or the number of dark pulse counts and to prevent fluctuations in dark current or number of dark pulse counts relative to the temperature, as a means therefor, cooling of a light receiving surface that accepts the weak light and cooling of a signal enforcement unit are performed. However, when giving such a method or the like as reported in Patent Literature 2 by way of example, there was such a problem that since cooling of the light receiving surface that is configured by an incidence window and a light receiving element frequently causes dew condensation, refraction and scattering of light occur to induce a loss of incident light amount.

Therefore, such necessity arises that in order to prevent fogging of the incidence window, a quartz window with defrosting heater is mounted onto a front stage of the incidence window of the light receiving surface and dry gas is sealed into between the quartz window with defrosting heater and the light receiving surface for heat insulation. Thereby, although a signal to noise ratio (SN) ratio is, needless to say, improved, it falls into such a trade-off relation that the light receiving surface goes away from a sample container that contains a luminescent substance and light recovery efficiency is reduced in many cases. Although the above-mentioned cooling form is, needles to say, effective for highly directive light, it leads to a loss of incident light amount in detection of light with no directivity such as chemiluminescence and bioluminescence in the sample.

In addition, a method of containing the entire device including parts for setting the light detector and the sample container in a cooler so as to cool the entire, instead of cooling of only the light detector is also conceivable. However, if the sample container that is an object to be measured and reagents containing enzymes that would induce the luminescent reaction are exposed to an environment of not more than 20° C., the reactivity will be remarkably reduced and therefore the amount of signals will be reduced. Accordingly, the present invention aims to provide a light detector and a system capable of improving the SN ratio and detecting luminescence with no directivity such as chemiluminescence and bioluminescence with high sensitivity.

Solution to Problem

As one aspect of the present invention in order to solve at least one of the above-mentioned problems, a plate member that holds a holder of a container for containing a sample, a light detector that detects luminescence in the aforementioned sample, a temperature control unit that performs control of a temperature of the aforementioned light detector, and a ventilator that performs air sending onto a light receiving surface of the aforementioned light detector are provided on a luminescence measuring device.

Advantageous Effects of Invention

According to the present invention, it becomes possible to measure bioluminescence highly sensitively and quantitatively by suppressing the noise and by suppressing temperature-derived variations in background signal of the reagent.

Problems, configurations and advantageous effects other than the above will be clarified by the following description of embodiments.

BRIEF DESCRIPTION OF DRAWINGS

FIG. 1A is a diagram showing one example of a general configuration of a weak luminescence measuring device according to an embodiment 1.

FIG. 4C is a plan view showing one example of the constant temperature dry air supply system according to the embodiment 4.

DESCRIPTION OF EMBODIMENTS

Figure 1B:
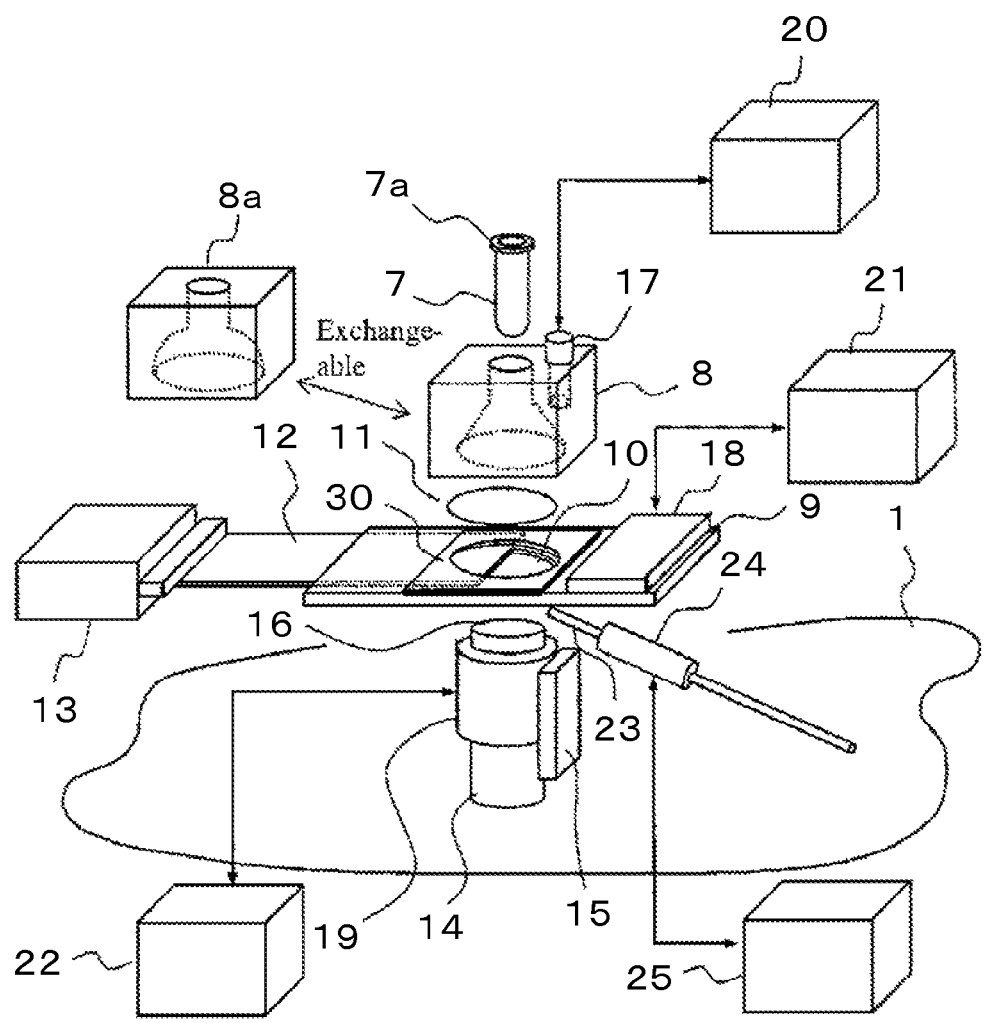
FIG. 1B is an exploded diagram showing one example of a configuration of the inside of the weak luminescence measuring device main body according to the embodiment 1.

In the following, embodiments of the present invention will be described with reference to the drawings. However, it is to be noted that the present embodiments are merely examples for implementing the present invention and do not limit the present invention. In addition, the same reference numerals are assigned to configurations that are common among the respective drawings.

Embodiment 1

Figure 1C:
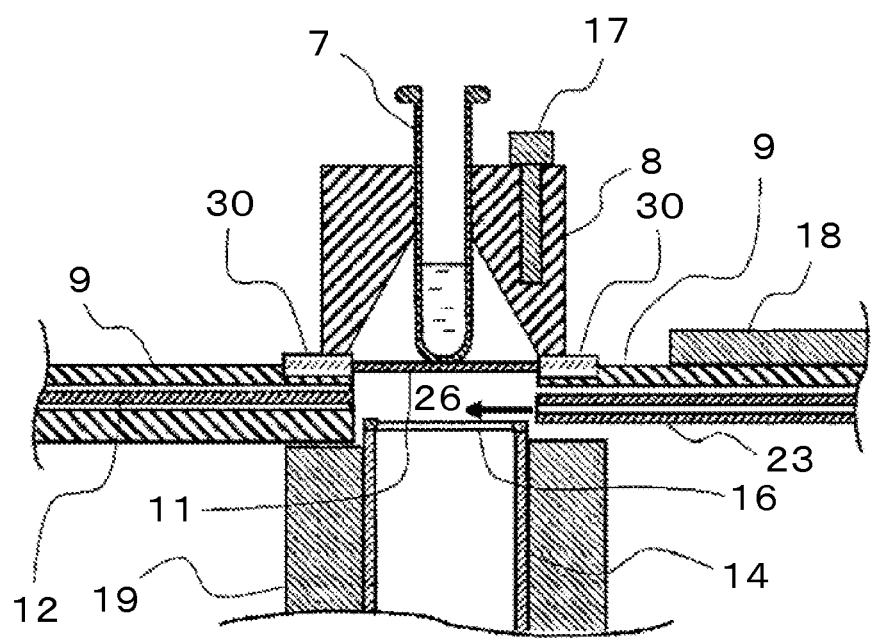
FIG. 1C is a sectional diagram showing one example of the configuration of the inside of the weak luminescence measuring device main body according to the embodiment 1.
Figure 1C:
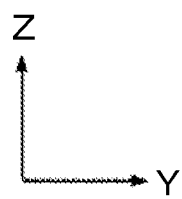

FIG. 1A, FIG. 1B, FIG. 1C are examples showing a configuration in a measuring room 5 of a weak luminescence measuring device pertaining to the embodiment 1. FIG. 1A is an outside view of a system configured by a weak luminescence measuring device main body 1, a compressor 2 that generates compressed air and a control device 3 that controls it. FIG. 1A, the weak luminescence measuring device main body 1 is a light shielded housing and is further configured by the measuring room 5 that has contained various drive mechanical components and a control room 6 that has contained various control devices. It is provided with an open/close door 4 that opens and closes when setting a sample container 7 shown in FIG. 1B. The device configuration of the inside thereof is as shown in FIG. 1B, FIG. 1C.

FIG. 1B shows an exploded diagram and FIG. 1C shows a sectional diagram of the assembled one. The sample container 7 is set into a sample container holder 8. The sample container holder 8 is installed into a through-hole 10 part in a first plate member 9. As material qualities of the first plate member 9, the material qualities that are high in thermal conductivity are selected. For example, they are aluminum, stainless steel, copper, gold, silver and so forth. In addition, in order not to store and reflect light in and from the first plate member 9, the surface of a metal material quality may be coated by alumite treatment and so forth so as to have a black surface.

The sample container holder 8 is made to be positioned simply by putting it on the first plate member 9. For example, a frame that allows fixed-position installation may be attached to the first plate member 9, or a circular groove, a square groove or the like into which a bottom part of the sample container holder 8 would be held may be inscribed in the first plate member 9 so as to fit the sample container holder 8 into it.

As shown in FIG. 1B, FIG. 1C, the sample container holder 8 is of a structure that the inside is hollowed out into a columnar part, and a conical part and a hemispherical part (8a) for supporting an outer periphery of the sample container 7, and the structure that an upper part and a lower part of the sample container holder 8 pass through it.

The sample container 7 is inserted into it through an upper small-diameter columnar opening and a pileus structure 7a on a container upper part is utilized for fixing it. Thereby, it is mounted onto the sample container holder 8 in a hanging-down state. In addition, in a case where the sample container 7 having no pileus structure 7a on the container upper part is to be used, a dedicated stopper or the like (not shown) to be attached to the sample container 7 may be prepared. In addition, the bottom part of the sample container 7 may be also held by disposing a visible light region in a through-hole 10 part, specifically, a light transmission window 11 that is at least 90% in transmittance relative to light of wavelengths from 300 nm to 650 nm or from 410 nm to 650 nm in the first plate member 9.

The light transmission window 11 may be plate-shaped or lens-shaped. As the material qualities of the light transmission window 11, quartz glass, borosilicate glass, UV cut glass, potassium fluoride, lithium fluoride, barium fluoride, rock salt, zinc selenium, acryl, polycarbonate and so forth are preferable. In addition, in a case of adopting the lens-shaped one, a biconvex one, a plano-convex one, a convex meniscus one, cylindrical one and so forth are preferable. In addition, to cut light of wavelengths of not more than 410 nm is effective in order to cut electrostatic noise light, and in this case, a color filter that cuts light of not more than 410 nm may be affixed to the light transmission window 11, the material quality of the light transmission window 11, or a long pass filter, a color glass filter and so forth that pass visible light of at least 410 nm may be adopted for the light transmission window 11. Needless to say, these filers may be used by affixing to an upper surface (the sample container 7 side) of the light transmission window 11 or a lower surface (the light detector 14 side) of the light transmission window 11.

The first plate member 9 is a light shielding member and has a structured that a second plate member 12 that is also a light shielding member can be inserted into the inside thereof. The inserted second plate member 12 can move in a y-axis direction in a top plate by using a first actuator 13 to serve as a shutter for opening and closing the through-hole 10 by movement of the second plate member 12. The first actuator 13 of the type of controlling it, for example, by power supply or air supply can be used. Needless to say, although the second light shielding member 12 is not necessarily needed as long as the light shielding property of the open/close window 4 is sufficient, a phenomenon called light storage is induced by shining light on the light receiving surface 16 even when a high voltage is not applied to the light detector 14 and the light detector 16 is in an OFF state and this frequently leads to occurrence of fluctuations in dark current and number of dark pulse counts. The second plate member 12 serves to suppress it.

The light detector 14 is installed under the first plate member 9 leaving a minute gap relative to the first plate member 9 and the light transmission window 11. It is preferable that the minute gap be between 0.05 and 10 millimeters, and the narrower the gap is, the higher the incidence efficiency of light upon a light receiving surface 16 becomes.

As shown in FIG. 1C, in order to precisely reproduce the minute gap, a position control means 15 may be used to store and control a position in a z-axis direction. The sample container 7, the sample container holder 8, the through-hole 10, the center of the light transmission window 11, the center of a light receiving surface 16 of the light detector 14 are aligned so as to be on the same axis in the z-axis direction. Incidentally, this alignment is generally executed when assembling the device. In addition, a space between the light detector 14 and the first plate member 9, the light transmission window 11 attached to the first plate member 9 may be exactly positioned when assembling the device or may be finely adjusted by using the position control means 15, and these can use the ones that perform control by using power supply type, air supply type actuators.

The movement control means 15 that has used the power supply type actuator is the one that is mainly configured by a rotation motor and a ball screw that converts rotation of the motor into linear motion, and a stage on which the light detector 14 is to be disposed. The light detection 14 on the stage that moves on the ball screw when a signal of a designated rotation pulse amount has been given can be moved to a target position with repeat accuracy of not more than ±10 microns, setting an origin that has been defined in advance by a sensor as a standard position.

In the air supply type actuator, the light detector 14 on the stage is moved by supplying compressed air of at least 0.1 kPa and a check plate or the like is disposed on a part of a member that operates together with the light detector 14 for positioning and the position is controlled by physically and forcibly stopping it by the check plate. It is possible to vertically move the light detector 14 by controlling supply of the compressed air by a valve.

In general, it is favorable to use a Photomultiplier Tube (PMT) and an Image Intensifier (I.I.) as the light detector 14 as far as the sensitivity is concerned. However, in a case where, though not meeting the sensitivity that would be equivalent to that of the PMT and the I.I., importance is to be attached to cost reduction and so forth of the device, it may be a semiconductor element such as a photodiode and so forth. However, in the present specification, only a system that has used the PMT will be described as one example of these light detectors 14.

The weak luminescence measuring device main body 1 is provided with at least one or more constant temperature controllers. In FIG. 1B, FIG. 1C, the sample container holder 8 is provided with a first constant temperature controller 17, the first plate member is provided with a second constant temperature controller 18, the light detector 14 is provided with a third constant temperature controller 19, a constant temperature dry air blast nozzle 23 is provided with a fourth constant temperature controller. The first incubator controller 17 is to be inserted into or mounted onto the container holder 8. The first constant temperature 17 is the one that an incubator and a temperature measuring machine adapted to always monitor the temperature of the container holder 8 that has been temperature-adjusted by the incubator and perform feedback of a supply power amount to the incubator that is necessary to maintain it at a fixed temperature, specifically, a thermocouple, a thermistor have been inserted into or mounted onto the container holder 8 that is a metal member made of aluminum, stainless steel, copper and so forth. These are to be controlled by a first constant temperature controller driver 20 that is contained in the control room 6 of the weak luminescence measuring device main body 1 and temperature setting thereof is arbitrarily possible via the control device 3. The first constant temperature controller 17 operates so as to maintain a fixed temperature, for example, within a range from room temperature to 40° C. by the first constant temperature control driver 20.

The second constant temperature controller 18 is to be inserted into or mounted onto the first plate member 9. The second constant temperature controller 18 maintains the first plate member 9 that is a metal material quality part made of aluminum, stainless steel, copper and so forth at a fixed temperature. It is the one that a temperature measuring machine that is necessary to always monitor the temperature of the first plate member 9 that has been temperature-adjusted by an incubator and perform feedback of a supply power amount to the incubator that is necessary to maintain it at a fixed temperature, specifically, a thermocouple, a thermistor have been inserted into or mounted onto it. These are to be controlled by a second constant temperature controller driver 21 that is contained in the control room 6 of the weak luminescence measuring device main body 1 and temperature setting thereof is arbitrarily possible via the control device 3. The second constant temperature controller 18 operates so as to maintain a fixed temperature, for example, within a range from 0° C. to 40° C.

The third constant temperature controller 19 is to be mounted onto the light detector 14. The third constant temperature controller 19 maintains the light detector 14 at a fixed temperature via a metal member made of aluminum, stainless steel, copper and so forth. It is the one that a temperature measuring machine that is necessary to always monitor the temperature of the light detector 14 that has been temperature-adjusted by an incubator and perform feedback of a supply power amount to the incubator that is necessary to maintain it at a fixed temperature, specifically, a thermocouple, a thermistor have been inserted into or mounted onto it. These are to be controlled by a third constant temperature controller driver 22 that is contained in the control room 6 of the weak luminescence measuring device main body 1 and temperature setting thereof is arbitrarily possible via the control device 3. The third constant temperature controller 17 operates so as to maintain a fixed temperature, for example, within a range from 0° C. to 40° C.

The fourth constant temperature controller 24 is a means for maintaining the temperature of the constant temperature dry air blast nozzle 23 fixedly. The fourth constant temperature controller 24 maintains the constant temperature dry air blast nozzle 23 at a fixed temperature via a metal member made of aluminum, stainless steel, copper and so forth. It is the one that a temperature measuring machine that is necessary to always monitor the temperature of the constant temperature dry air blast nozzle 23 that has been temperature-adjusted by an incubator and perform feedback of a supply power amount to the incubator that is necessary to maintain it at a fixed temperature, specifically, a thermocouple, a thermistor have been inserted into or mounted onto it. These are to be controlled by a fourth constant temperature controller driver 25 that is contained in the control room 6 of the weak luminescence measuring device main body 1 and temperature setting thereof is arbitrarily possible via the control device 3. The fourth constant temperature controller 17 operates so as to maintain a fixed temperature, for example, within a range from 0° C. to 40° C.

As shown in FIG. 1C, a temperature-adjusted air blast (constant temperature dry air 26) to be supplied from the constant temperature dry air blast nozzle 23 is disposed in parallel with a plane direction of the light receiving surface 16 such that it flows in parallel with the light receiving surface 16 of the light detector 14. It is good to keep the constant temperature dry air 26 flowing also before luminescence measurement and during luminescence measurement. Specifically, supply of the constant temperature dry air 26 is started simultaneously with start-up of the weak luminescence measuring device main body 1 and the control device 3. The control device 3 is controlled such that luminescence measurement cannot be started for a time taken until the temperature reaches a set temperature of the constant temperature dry air blast nozzle 23 and is fixed. Needless to say, in a case where it is desired to stop supply of the constant temperature dry air 26 as a countermeasure against occurrence of a trouble, supply stop can be selected from the control device 3.

In addition, at termination of luminescence measurement, that is, when stopping the device, the constant temperature dry air 26 is controlled to stop after the first constant temperature controller 17, the second constant temperature controller 18, the third constant temperature controller 19, the fourth constant temperature controller 24 have been stopped and then each constant temperature controller becomes the same as the temperature in the device. Thereby, generation of dew condensation can be prevented. Although, with regard to control of the constant temperature dry air 26, there is also a method of air-tightly retaining dry air in advance and controlling the temperature by the third constant temperature controller 19 of the light detector 14, a thickness of a constant temperature dry air layer of at least several mm or more is needed for heat insulation against an internal ner-temperature of the weak luminescence measuring device 1.

On the other hand, in a form of keeping it flowing by the open system as in the present embodiment, since the constant temperature dry air 26 is always replaced, the air capacity for heat insulation is effectively increased. Accordingly, even when a gap between the light receiving surface 16 and the light transmission window 11 of the light detector 14 is as very narrow as about 0.1 mm, heat exchange is efficiently possible. In addition, it is preferable to utilize laminar flow ventilation that sends air to a narrow region in parallel because the air mixing rate is bad. Since the air mixing rate is bad, efficiency of replacement with air in a supply region of the constant temperature dry air 26 is high and air can be replaced in a short time. Further, a configuration that air is sent in parallel also has such an advantage that pressures imposed on the light transmission window 11 and the light receiving surface 16 can be lightened.

Figure 3A:
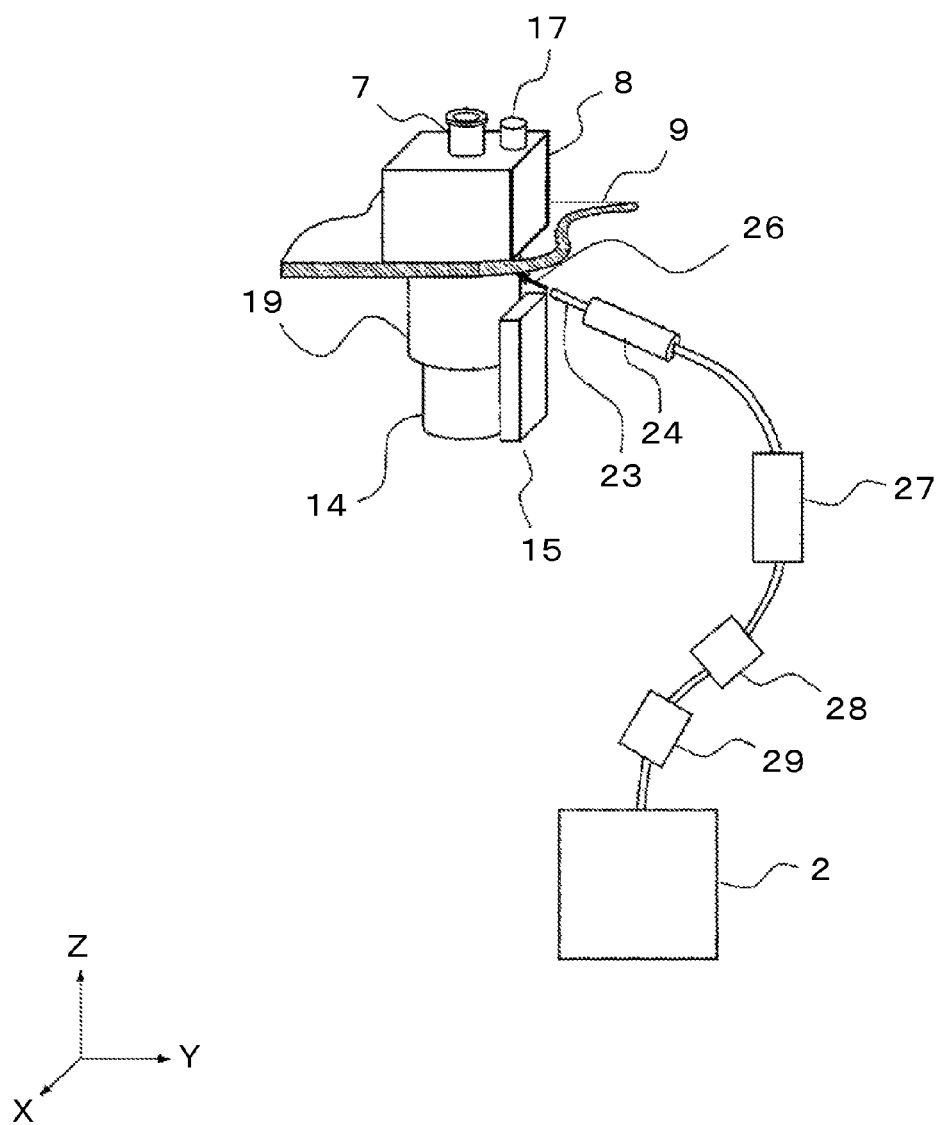
FIG. 3A is a diagram showing one example of a constant temperature dry air supply system according to the embodiment 1.

FIG. 3A is a diagram showing a supply system for the constant temperature dry air 26. This blast supply system is configured by the constant temperature dry air blast nozzle 23, the fourth constant temperature controller 24, an air dryer 27, a first filter 28, a second filter 29, and the compressor 2. The air supplied from the compressor 2 first passes through the second filter 29, the first filter 28 that are means for removing impurities such as garbage, oil constituents and so forth and then passes through the air dryer 27 that is a means for removing water. This dry air is controlled to a fixed temperature by temperature adjustment of the fourth constant temperature controller 24 and is supplied so as to flow in parallel with a plane of the light receiving surface 16 of the light detector 14.

The constant temperature dry air 26 is a means for avoiding dew condensation on the light receiving surface 16 that would generate when its temperature is lower than the internal temperature of the measuring room 5 of the weak luminescence measuring device main body 1 and a difference between these temperatures is large. The constant temperature dry air blast nozzle 23 is important in a case where in the first constant temperature controller 17, the constant temperature controller 18, the third constant temperature controller 19, in particular, the third constant temperature controller 19 is to be set lower than the room temperature and the constant temperature dry air 26 supplied from the constant temperature dry air blast nozzle 23 makes it possible to prevent dew condensation on the surface of the light receiving surface 16, to avoid light scattering caused by water drops on the light receiving surface 16 and to suppress the fluctuations in optical signal caused by a loss of the incident light amount.

As shown in FIG. 1B, FIG. 1C, the temperature of the sample container holder 8 and the temperature of the first plate member 9 can be controlled independently by disposing the sample container holder 8 that has been temperature-adjusted by the first constant temperature controller 17 on a heat insulation member 30 on the first plate member 9 (FIG. 1C). It is preferable that the heat insulation member 30 be a plate member that has a through-hole that is equal or more than the through-hole 10 and is wider than a bottom face part of the sample container holder 8. In addition, as shown in FIG. 1C, a depression for disposing the heat insulation member 30 may be provided in the first plate member 9 so as to fit the heat insulation member 30 into it.

In general, in chemiluminescence and bioluminescence using an enzyme, the enzyme activity that contributes to a luminescent reaction is high and light generation efficiency is high at from 20° C. to 40° C. On the other hand, since cooling of the light detector 14 and the light receiving surface 16 thereof enables the dark current and the number of dark pulse counts to be reduced and results in a reduction in noise level, it is preferable to lower the temperatures. Thus, it is necessary to temperature-adjust the temperature set values of the first constant temperature controller 17 and the second constant temperature controller 18 and the third constant temperature controller 19 in accordance with various applications, it is effective to provide the heat insulation member 30 for heat insulation between the sample container holder 8 and the first plate member 9, and heat insulation against the light detector 14 becomes possible by air heat insulation that uses air present between the sample container holder 8 and the first plate member 9.

The material qualities of the heat insulation member 30 are resinous materials or fibrous materials and further foamed ones and are urethane resins, phenol resins, polyethylene resins, EPS cellulose fibers, glass fibers, carbonized corks and so forth. Needless to say, also a form that the heat insulation member 30 is not used daringly is preferable in a case where the efficiency is good even when a photoreaction temperature is not more than the room temperature and the sample container holder 8, the first plate member 9, the light detector 14 may be subjected to constant temperature control at the same temperature.

In a case of cooling the light detector 14 by the third constant temperature controller 19, it is important to make the temperature of the light detector 14 and the temperature of the light receiving surface 16 the same as each other for prevention of dew condensation and reductions in dark current, number of dark pulse counts. Therefore, a way of use that the set temperature of the fourth constant temperature controller 24 and the set temperature of the third constant temperature controller 19 are made the same as each other is preferable in the present embodiment. Further, cooling of the first plate member 9 by the second constant temperature controller 18 reduces a temperature gradient caused by a temperature difference between the constant temperature dry air 26 discharged from the constant temperature dry air blast nozzle 23 and the device inside and the cooling efficiency of the light receiving surface 16 is improved.

Figure 10:
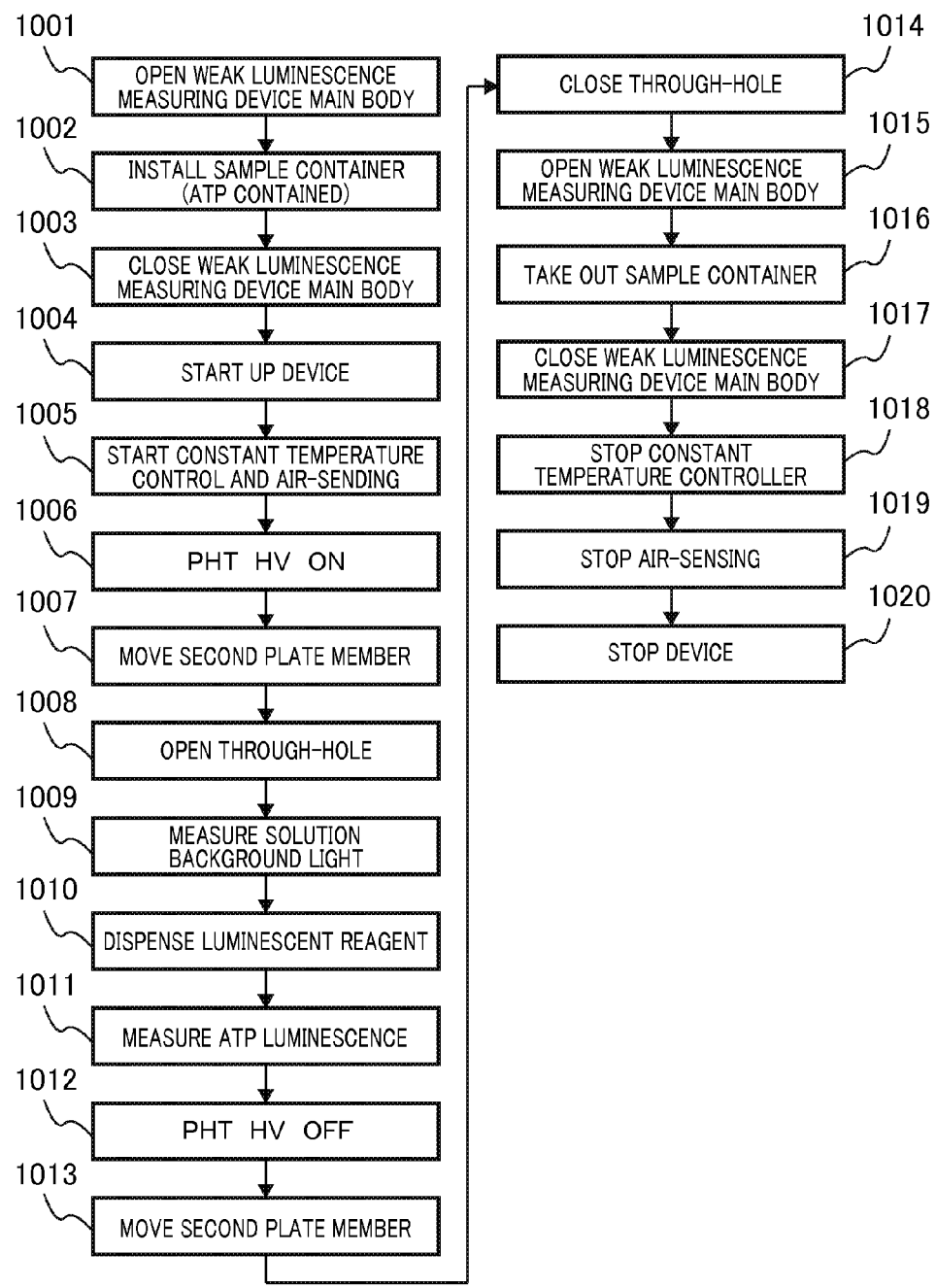
FIG. 10 is a flowchart showing one example of measurement procedures of luminescence measurement according to the embodiment 1.

FIG. 10 is a flowchart for describing one example of measurement procedures of luminescence measurement. First, the open/close door 4 of the weak luminescence measuring device main body 1 is opened (S1001), the sample container 7 that an ATP solution has been stocked is installed (S1002). After installation, the open/close door 4 is closed (S1003). Then, start-up of the weak luminescence measuring device main body 1 and the control device 3 is performed (S1004), constant temperature control by the first constant temperature controller 17, the second constant temperature controller 18, the third constant temperature controller 19, the fourth constant temperature controller 24 is started and supply of the constant temperature dry air 26 is started (S1005). Next, HV is applied to the light detector 14 (S1006). Then, when the temperature of the constant temperature dry air 26 reaches the set temperature of the constant temperature dry air blast nozzle 23, the second plate member 12 is moved (S1007) and the through-hole 10 is opened to make the light receiving surface 16 face the sample container 7 via the light transmission window 11 (S1008). Thereafter, measurement is started. The constant temperature dry air 26 is kept flowing also during luminescence measurement.

Measurement is started before a luminescent reagent is dispensed from a dispensing machine and background light measurement in the sample container 7 is performed (S1009). After background light measurement has been performed for a certain fixed time, the luminescent reagent is dispensed from the dispensing machine (S1010). The luminescent reagent reacts with ATP in the sample container and a luminescent reaction is started in the container. After luminescence measurement of ATP has been performed for a certain fixed time (S1011), HV of the light detector 14 is turned OFF (S1012), the second plate member 12 is moved to the position before start of measurement (S1013) and the through-hole 10 is closed (S1014). Next, the open/close door 4 of the weak luminescence measuring device main body 1 is opened (S1015) in order to take out the measured sample container 7, the sample container 7 is taken out (S1016). In a case where it is desired to measure the next sample, it is newly installed in this process and the above-described measurement flow is repeated.

In a case of terminating measurement, after the sample container 7 has been taken out, the open/close door 4 of the weak luminescence measuring main body 1 is closed (S1017). Then, the first constant temperature controller 17, the second constant temperature controller 18, the third constant temperature controller 19, the fourth constant temperature controller 24 are stopped (S1018), and thereafter the constant temperature dry air 26 is stopped after each constant temperature controller has been equalized with the temperature in the device (S1019). Finally, stopping of the weak luminescence measuring device main body 1 and the control device 3 is performed (S1020).

Owing to the above, it becomes possible for the light detector to bring its light receiving surface close to the sample container that contains the luminescent substance and to prevent dew condensation caused by cooling of the light receiving surface while maintaining the sample container and the reagents that contain the enzymes which would induce the luminescent reaction at a so-called optimum temperature of at least 20° C. at which their activities will be high. Then, it becomes possible to measure bioluminescence from an extremely low concentration molecule highly sensitively and quantitatively by the proximity effect of the measurement sample container bottom face, simultaneously with suppression of noise and the temperature-derived fluctuations in background signal of the sample, and for example, weak light of the ATP luminescence in one bacterium can be measured with high sensitivity and high precision.

Embodiment 2

Figure 2A:
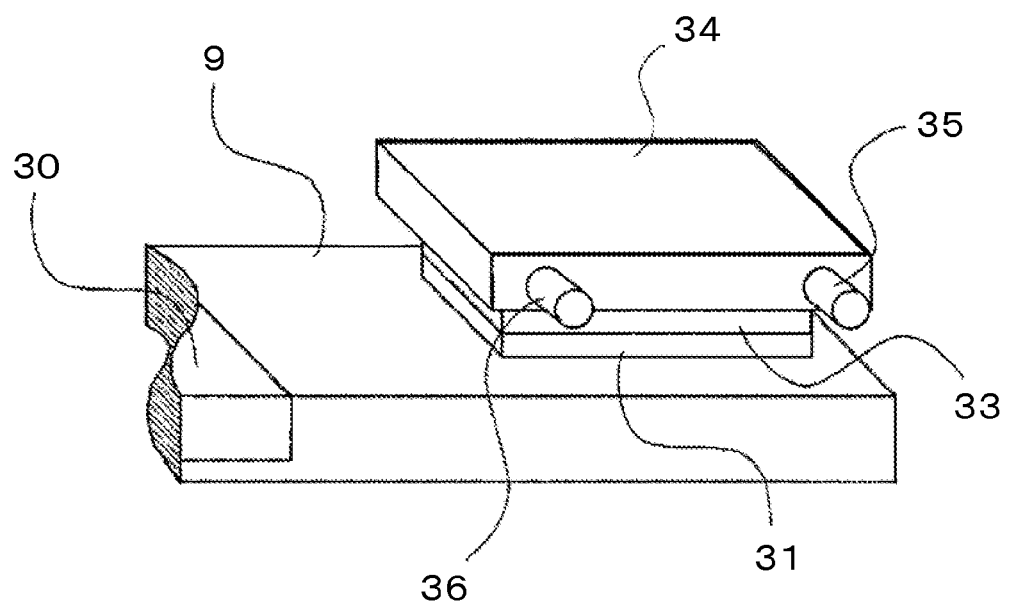
FIG. 2A is a diagram showing one example of a configuration using an electronic cooling element for constant temperature control of a first plate member.

It is preferable to use electronic cooling elements (Peltier elements) in the second constant temperature controller 18, the third constant temperature controller 19, the fourth constant temperature controller 24 in order to set the set temperatures of the second constant temperature controller 18, the third constant temperature controller 19, the fourth constant temperature controller 24 to not more than 10° C. FIG. 2A shows a configuration diagram of the second constant temperature controller 18 of the first plate member 9 when a first electronic cooling element has been used. Here, the second constant temperature controller 18 is configured by a cooling surface 31 of the electronic cooling element, a heat radiating surface 33 of the first electronic cooling element, a first heat discharger 34, a first cooling medium introduction port 35, a first cooling medium discharge port 36 that will be described in the following by using FIG. 2A.

As shown in FIG. 2A, in the electronic cooling element, a surface that is opposite to the cooling surface 31 of the first thermoelectric cooling element and is not in contact with the first plate member 9 serves as the so-called heat radiating surface 33 of the first electronic cooling element from which heat drawn by cooling is radiated. In order to prevent destabilization of constant temperature control caused by temperature rising of the measuring room 5 of the weak luminescence measuring device main body 1, heat of the heat radiating surface 33 of the first electronic cooling element may be discharged from the weak luminescence measuring device main body 1 to the control room 6 and the outside by supplying cooling gas or cooling water. In addition, the first heat discharger 34 is a heat discharger that has been attached to the heat radiating surface 33 of the first electronic cooling element used for cooling the first plate member 9 and is provided with the first cooling medium introduction port 35 and the first cooling medium discharge port 36. The first heat discharger 34 is a plate member that is high in thermal conductivity and it is preferable to use metals such as aluminum, stainless steel, copper, gold, silver and so forth.

A flow path that connects together the first cooling medium introduction port 35 and the first cooling medium discharge port 36 is formed in the first heat discharger 34 and is configured that the cooling medium flows along a route concerned as described later, and the route concerned is as shown by a dotted line on the first heat discharger 34 in FIG. 2D.

Figure 2B:
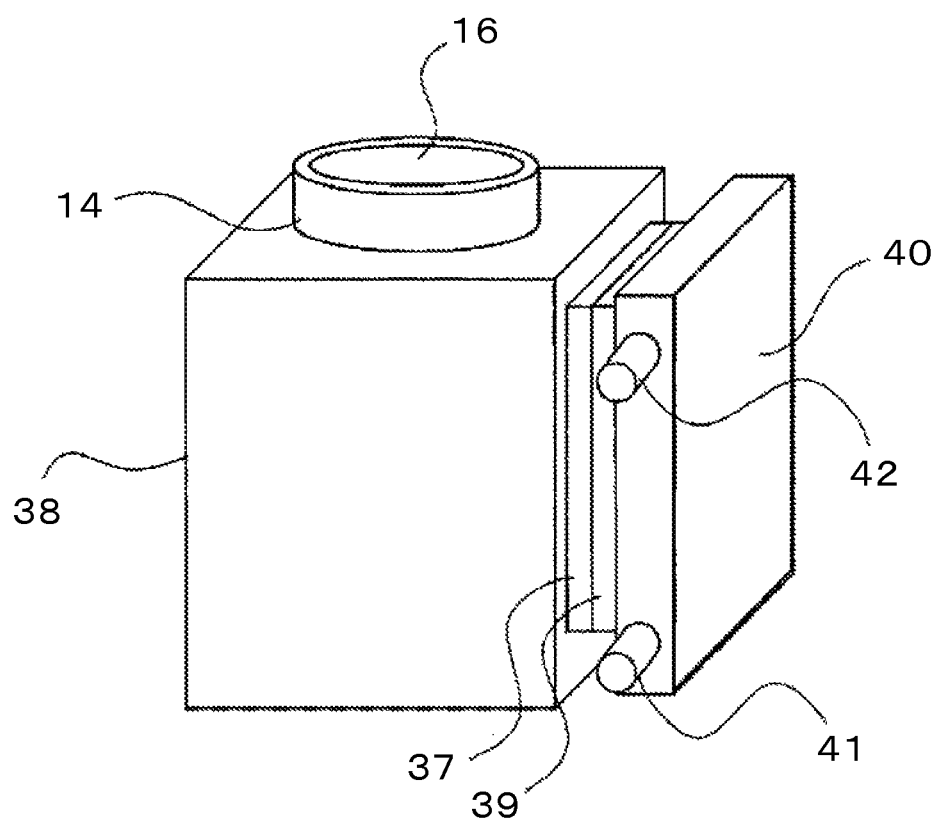
FIG. 2B is a diagram showing one example of a configuration using the electronic cooling element for constant temperature control of a light detector.

FIG. 2B shows a configuration diagram of the third constant temperature controller 22 of the light detector 14 when a second electronic cooling element has been used. Here, the third constant temperature controller 22 is configured by a first metal block 38, a cooling surface 37 of the second electronic cooling element, a heat radiating surface 39 of the second electronic cooling element, a second heat discharger 40, a second cooling medium introduction port 41, a second cooling medium discharge port 42 that will be described in the following by using FIG. 2B.

As shown in FIG. 2B, in the electronic cooling element, a surface that is opposite to the cooling surface 37 of the second electronic cooling element that is in contact with the first metal block 38 for cooling the light detector 14 serves as the so-called heat radiating surface 39 of the second electronic cooling element from which heat drawn by cooling is radiated. In order to prevent destabilization of constant temperature control caused by temperature rising of the measuring room 5 of the weak luminescence measuring device main body 1, heat of the heat radiating surface 39 of the second electronic cooling element may be discharged from the weak luminescence measuring device main body 1 to the outside by supplying cooling gas or cooling water.

The second heat discharger 40 is a heat discharger that has been attached to the heat radiating surface 39 of the second electronic cooling element used for cooling the light detector 14 and is provided with the second cooling medium introduction port 41 and the second cooling medium discharge port 42. The second heat discharger 40 is a plate member that is high in thermal conductivity and it is preferable to use metals such as aluminum, stainless steel, copper, gold, silver and so forth. A flow path that connects together the second cooling medium introduction port 41 and the second cooling medium discharge port 42 is formed in the second heat discharger 40 and is configured that the cooling medium flows along a route concerned as described later, and the route concerned is as shown by a dotted line on the second heat discharger 40 in FIG. 2D.

Figure 2C:
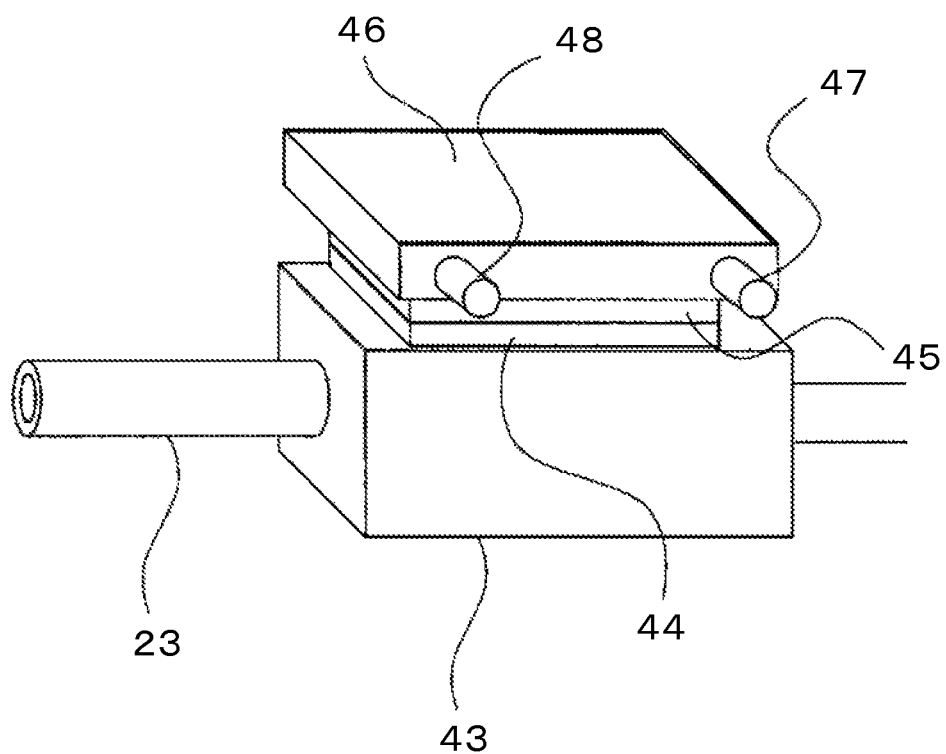
FIG. 2C is a diagram showing one example of a configuration for cooling a heat discharger.

FIG. 2C shows a configuration diagram of the fourth constant temperature controller 24 of the constant temperature dry air blast nozzle 23 when a third electronic cooling element has been used. Here, the fourth constant temperature controller 24 is configured by a second metal block 43, a cooling surface 44 of the third electronic cooling element, a heat radiating surface 45 of the third electronic cooling element, a third heat discharger 46, a third cooling medium introduction port 47, a third cooling medium discharge port 48 that will be described in the following by using FIG. 2C. As shown in FIG. 2C, in the electronic cooling element, a surface that is opposite to the cooling surface 44 of the third electronic cooling element that is in contact with the second metal block 43 for cooling the constant temperature dry air blast nozzle 23 serves as the so-called heat radiating surface 45 of the third electronic cooling element from which heat drawn by cooling is radiated. In order to prevent destabilization of constant temperature control caused by temperature rising of the measuring room 5 of the weak luminescence measuring device main body 1, heat of the heat radiating surface 45 of the third electronic cooling element may be discharged from the weak luminescence measuring device main body 1 to the outside by supplying cooling gas or cooling water.

The third heat discharger 46 is a heat discharger that has been attached to the heat radiating surface 45 of the third electronic cooling element used for cooling the constant temperature dry air blast nozzle 23 and is provided with the third cooling medium introduction port 47 and the third cooling medium discharge port 48. The third heat discharger 46 is a plate member that is high in thermal conductivity and it is preferable to use metals such as aluminum, stainless steel, copper, gold, silver and so forth. A flow path that connects together the third cooling medium introduction port 47 and the third cooling medium discharge port 48 is formed in the third heat discharger 46 and is configured that the cooling medium flows along a route concerned as described later, and the route concerned is as shown by a dotted line on the third heat discharger 46 in FIG. 2D.

Figure 2D:
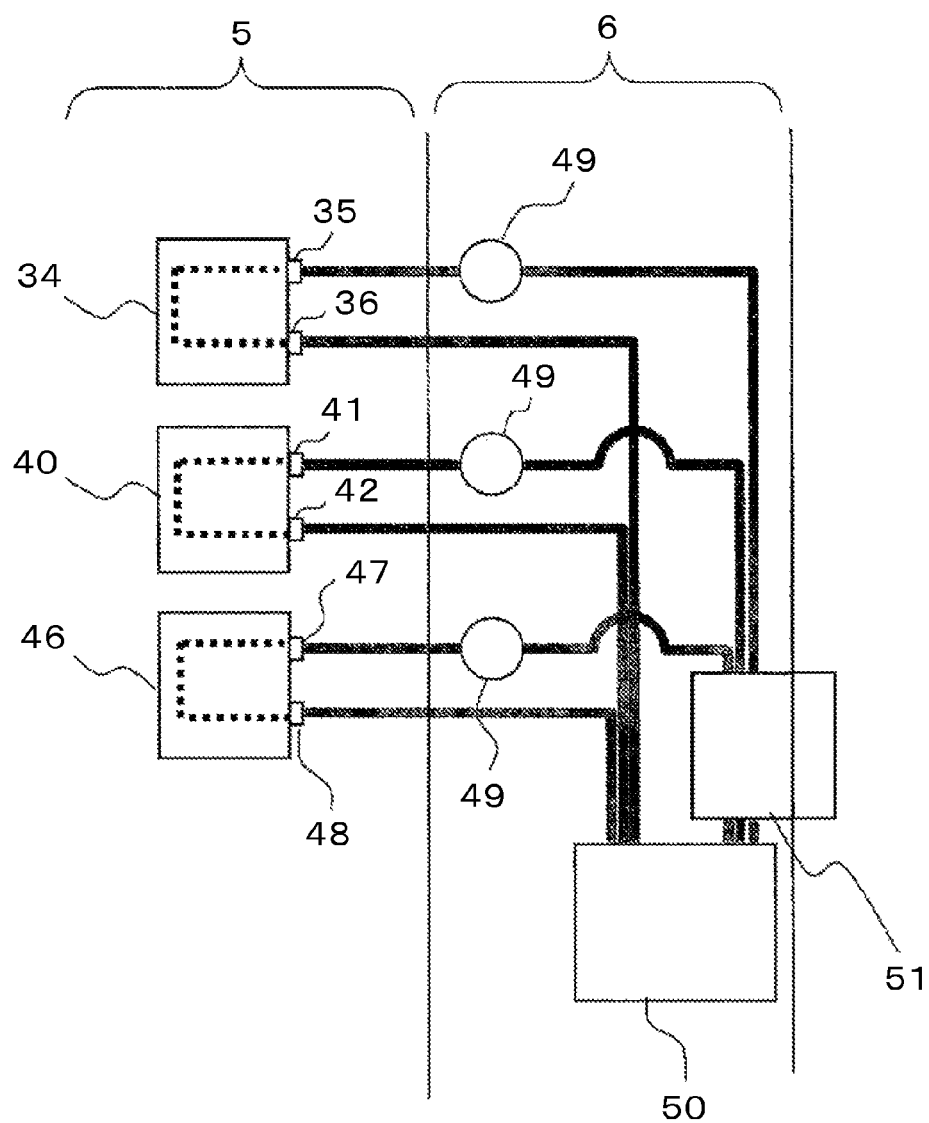
FIG. 2D is a block diagram of a configuration for solution-sending and circulating a cooling medium to and through the heat discharger.

FIG. 2D shows a typical example of a block diagram of a configuration that the cooling medium is liquid-sent to and circulated through the first heat discharger 34, the second heat discharger 40, the third heat discharger 46 in FIG. 2A, FIG. 2B, FIG. 2C. The cooling medium is guided from a cooling medium storage tank 50 to the first cooling medium introduction port 35, the second cooling medium introduction port 41, the third cooling medium introduction port 47 of the first heat discharger 34, the second heat discharger 40, the third heat discharger 46 by using a circulation type pump 49, the cooling medium is sent to the respective flow paths of the first heat discharger 34, the second heat discharger 40, the third heat discharger 46 and is returned to the cooling medium storage tank 50 from the first cooling medium discharge port 36, the second cooling medium discharge port 42, the third cooling medium discharge port 48 while drawing heat. If the temperature of the coolant storage tank 50 rises with the drawn heat, a cooler 51 may be prepared so as to maintain a cooling medium supply line at a constant temperature.

It is preferable to use a diaphragm pump and a peristaltic pump as the circulation type pump 49. Although 49, 50, 51 are configured by the measuring room 5 and the control room 6 of the weak luminescence measuring device main body 1, the circulation type pump 49, the cooling medium storage tank 50, the cooler 51 may be installed in the control room 6 or on the outside of the weak luminescence measuring device main body 1. Although the above one is an example that a liquid has been used as the cooling medium, gas may be also used. However, the liquid, in particular, water is more preferable from the viewpoint of the high level of thermal conductivity thereof. Although fresh water may be also allowable, an antifreezing solution that contains ethylene glycol may be also used.

On the other hand, only circulation of the cooling medium may be used as a means for cooling the second constant temperature controller 18, the third constant temperature controller 19. The cooling medium storage tank 50 and the cooler 51 may be prepared so as to form the cooling medium introduction port, the cooling medium discharge port and the flow path that connects them together in the first plate member 9, the cooling medium introduction port, the cooling medium discharge port and the flow path that connects them together in the first metal block 38, the cooling medium introduction port, the cooling medium discharge port and the flow path that connects them together in the second metal block 43 by using the diaphragm pump and the peristaltic pump, thereby circulating the cooling medium as in the embodiment in FIG. 2D. Although in a case where cooling with circulating water is utilized, the electronic cooling element is no longer needed and the configuration is simplified, in a case where importance is to be attached to precision, stability of temperature control, it is preferable to use the electronic cooling element. In addition, although fresh water may be also allowable as cooling water, in a case where it is desired to control at near 0° C., it is preferable to use the antifreezing solution that contains ethylene glycol.

Although the second constant temperature controller 18, the third constant temperature controller 19, the fourth constant temperature controller 24 have been described so far from the viewpoint of cooling, needless to say, temperature rising is also possible in order to set at a fixed temperature from the viewpoint of constant temperature. The temperature may be risen by warm water circulation or by changing the polarity of the electronic cooling element. In a case where the installation place of the device is at a low temperature, it may be necessary in some cases. In addition, in regard to dew condensation caused by cooling, in a case where dew condensation has generated by any possibility, the polarity of the electronic cooling element is changed and heating is performed. Presence/absence of dew condensation may be detected by installing a water leakage sensor.

A sectional shape of the flow paths that the cooling medium flows in the first heat discharger 34, the second heat discharger 40, the third heat discharger 46 may be any one of a circle, a square, a triangle and so forth and there is no particular limitation on the flow path length and the route of the flow path. However, the larger the percentage of the internal flow path volume in the total volume of the heat dischargers is, the better, and specifically, it is favorable that (the internal flow path volume)/(the total volume of the heat dischargers) be at least ⅓.

Embodiment 3

Figure 3B:
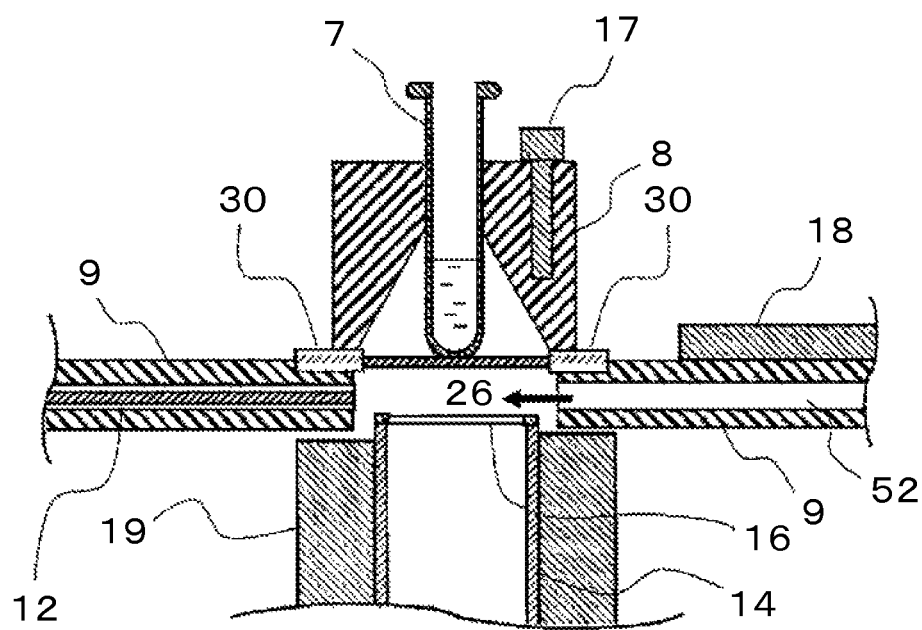
FIG. 3B is a diagram showing one example of a constant temperature dry air supply system according to an embodiment 3.
Figure 3C:
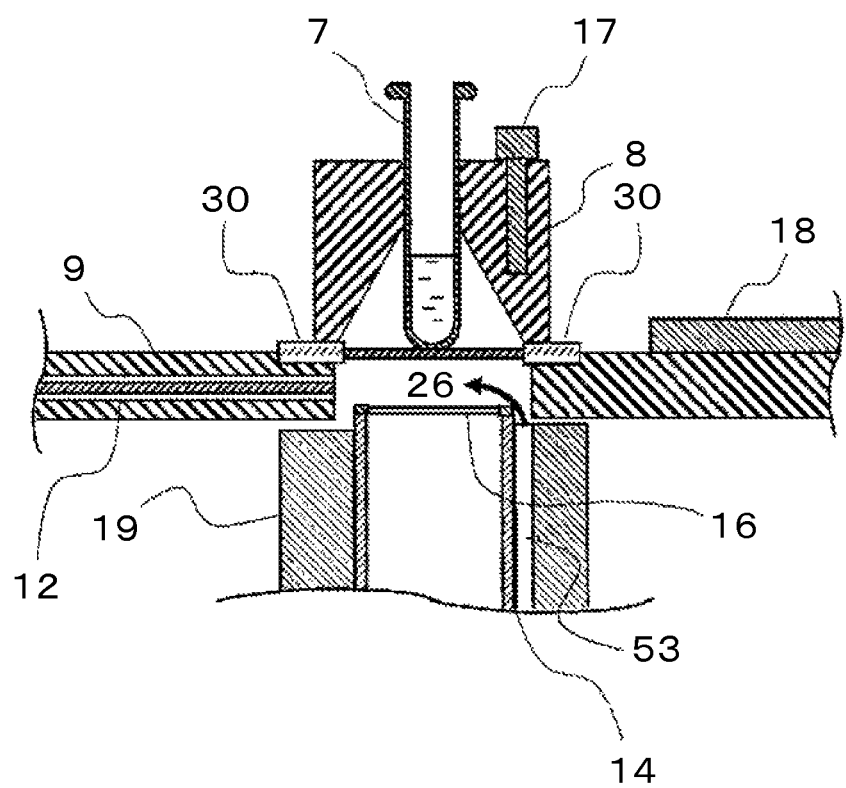
FIG. 3C is a diagram showing one example of the constant temperature dry air supply system according to the embodiment 3.

FIG. 3B and FIG. 3C show modified embodiments of a temperature adjusting method for the constant temperature dry air 26. Unlike FIG. 3A, they are forms not using the constant temperature dry air nozzle 23.

FIG. 3B is a method of forming a first blast flow path 52 in the first plate member 9, letting dry air flow into the first plate member 9 that has been temperature-adjusted by the second constant temperature controller 18 so as to adjust it to the same temperature as that of the first plate member 9, and letting the constant temperature dry air 26 flow in parallel with the light receiving surface 16. That is, the air that has been supplied from the compressor 2 passes through the second filter 29, the first filter 28, the air dryer 27 and thereafter this dry air is temperature-adjusted by passing through the blast flow path 52 in the first plate member 9 and is sent in parallel with the light receiving surface 16. Since temperature adjustment of the constant temperature dry air 26 is performed by the second constant temperature controller 18 of the first plate member 9, the control mechanism becomes easy and simple and the constant temperature dry air blast nozzle 23 and the fourth constant temperature controller 24 are no longer needed.

FIG. 3C is a method of forming a second blast flow path 53 in a temperature transfer member by effectively utilizing the temperature transfer member of the third constant temperature controller 19, and generating the constant temperature dry air 26 by introducing dry air into the second blast flow path. That is, the air that has been supplied from the compressor 2 passes through the second filter 29, the first filter, the air dryer 27, and thereafter this dry air is temperature-adjusted by passing through the second blast flow path 53 and is sent in parallel with the light receiving surface 16. Since temperature adjustment of the constant temperature dry air 26 is performed by the third constant temperature controller 19 of the first plate member 9, the control mechanism becomes easy and simple and the constant temperature dry air blast nozzle 23 and the fourth constant temperature controller 24 are no longer needed.

Here, a flow rate V (L/min) required for cooling is obtained from the following formula.

$$V \text{ (L/min)} = (P \times 3600)/(0.278 \times C \times d \times \Delta t)$$

In Formula (1), P is a supplied power mount (W) from the electronic cooling element, C is a specific heat (kJ/(kg·° C.)), d is a density (kg/m3) and Δ is a temperature difference. In the following, a case where the temperature of the dry air to be supplied is lowered from 25° C. to 5° C. will be considered. For simplicity, when calculating on the assumption that the power supply amount of the electronic cooling element P=50 W, C=1.007, d=1.2, Δt=20 as other parameters, it may be made to pass through within the flow path at not more than 2.1 mL/min, and the smaller the flow path sectional area is, the more efficiently it can be cooled. For example, it can be sufficiently cooled by passing it 210 mm in one minute with the section of 100 mm² of 10 mm each side. The same also applies in a case where the fourth constant temperature controller 24 of the embodiment 1 is used, and if the section is 100 mm², the fourth constant temperature controller 24 may have a temperature adjustment part of 210 mm. In a case where the light detector 14 that the diameter of the light receiving surface 16 is 25 mm has been used, a light received area is about 500 mm², in a case where a distance between it and the light transmission window 11 is 0.05 mm, a space volume formed by the light receiving surface 16 and the light transmission window 11 is 25 mm³ (=25 μl), in a case of 10 mm, the space volume amounts to 5000 mm³ (5 ml). In substitution of 5° C. for the entire volumetric space of them, it is necessary to change the supply flow rate in comparison of the case of 0.05 mm with the case of 10 mm and a difference of 100 times is generated. In addition, the larger the volume is, the more the temperature gradient is produced as it goes away from the outlet vicinity and the more the temperature difference is increased. Therefore, in order to minimize the temperature gradient, it is effective to increase the supply amount of the constant temperature air 26 or to cool a lower surface of the first plate member 9. In addition, in order to minimize the temperature gradient, the constant temperature dry air 26 may be supplied from a plurality of places toward the center.

In addition, in a case where the temperature of the dry air is to be lowered from 30° C. to 0° C. and in a case where the power supply amount is low and is 20 W, when a calculation is made by setting other parameters as C=1.007, d=1.2, Δt=20, it may be made to pass through within the flow path at not more than 0.6 mL/min. Incidentally, the thermal conductivity of the light receiving surface 16 of the light detector 14 is not taken into account in a result of the above-mentioned calculation. As for the surface material quality of the light receiving surface 16 of the light detector 14 that measures a visible light region, glass is general and in reality it is necessary to take 0.55-0.75 W/m·k into account as its thermal conductivity. However, since the glass plate on the surface of the light receiving surface 16 is very thin, the material dependence of heat transfer velocity by the thermal conductivity can be almost disregarded in cooling of the material of a photoelectric surface. In addition, since the light detector 14 controls it to the same temperature as that of the constant temperature dry air 16 by the third constant temperature controller 19, cooling from the inside of the light detector 14 is also added and there is no need to take the thermal conductivity of the material quality of the surface into account.

Embodiment 4

Figure 4A:
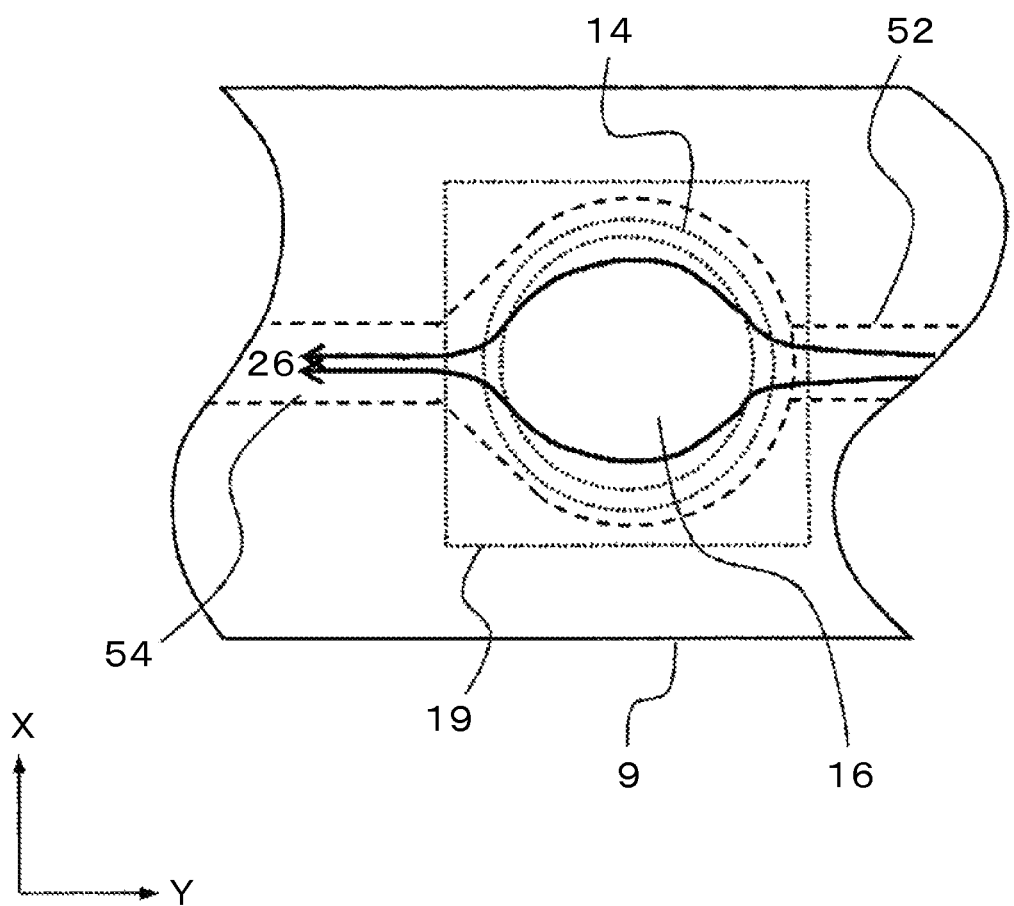
FIG. 4A is a plan view showing one example of a constant temperature dry air supply system according to an embodiment 4.
Figure 4B:
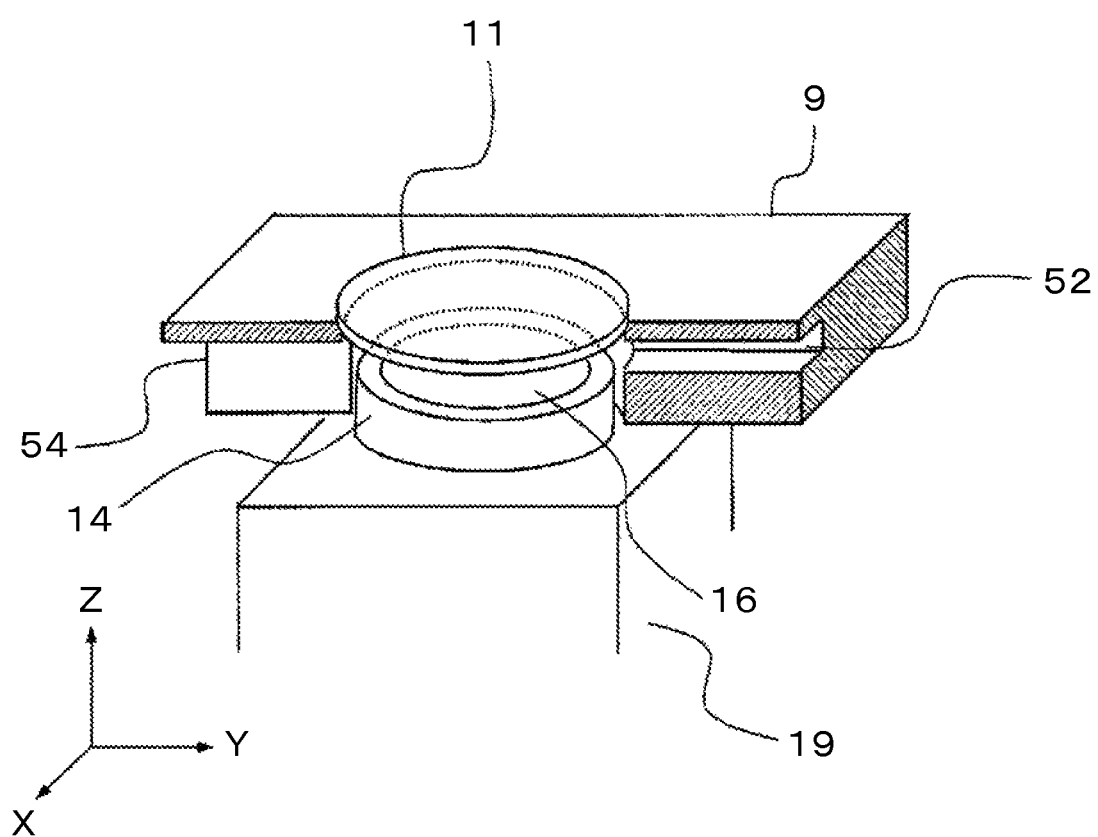
FIG. 4B is a cubic diagram showing one example of the constant temperature dry air supply system according to the embodiment 4.

In the present embodiment, a means for positively supplying the constant temperature dry air 26 to the light receiving surface 16 in a case where a gap between the light receiving surface 16 and the first plate member 9 or the light transmission window 11 to be mounted into the through-hole 10 in the first plate member 9 will be described. FIG. 4A, FIG. 4B, FIG. 4C, FIG. 4D are diagrams showing positional relations among a structure of a part into which the light detector 14 of the first plate member 9 is to be inserted, the light detector 14 and the light receiving surface 16. FIG. 4A, FIG. 4B are examples relevant to a form of supplying the constant temperature dry air 26 from the first blast flow path 52 provided in the first plate member 9 shown in FIG. 3B. If a counter bore 54 is formed in the first plate member 9 and a gap between leading ends of the light transmission window 11 and the light detector 14 is made slightly wider than a gap formed by an outer wall of the leading end part of the light detector 14 and a wall of the through-hole 10, the constant temperature dry air 26 can be positively sent from the first blast flow path 52 into the space between the light receiving surface 16 and the first plate member 9 or the light transmission window 11 and the constant temperature dry air 26 that has passed through the light receiving surface 16 will flow out into the counter bore 54.

Incidentally, the constant temperature dry air 26 marked with an arrow in FIG. 4A shows that the air flows in a direction shown by the arrow. FIG. 4B three-dimensionally shows the sections of the first blast flow path 52, the through-hole 10, the counter bore 54 of the first plate member 9 through which the constant temperature dry air 26 flows.

Figure 4D:
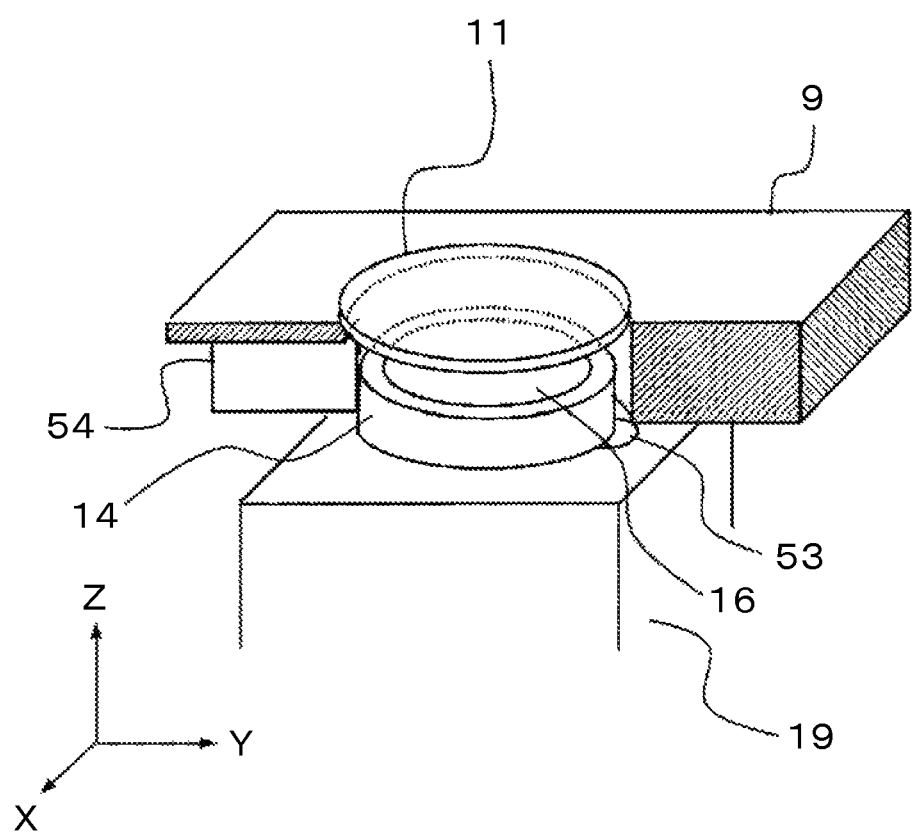
FIG. 4D is a cubic diagram showing one example of the constant temperature dry air supply system according to the embodiment 4.

FIG. 4C, FIG. 4D are examples relevant to a form of supplying the constant temperature dry air 26 from the second blast flow path 53 in the temperature transfer member of the third constant temperature controller 19 shown in FIG. 3C. If the counter bore 54 is formed in the first plate member 9 and the gap between leading ends of the light transmission window 11 and the light detector 14 is made slightly wider than the gap formed by the outer wall of the leading end part of the light detector 14 and the wall of the through-hole 10, the constant temperature dry air 26 can be positively sent from the second blast flow path 53 into the space between the light receiving surface 16 and the first plate member 9 or the light transmission window 11 and the constant temperature dry air 26 that has passed through the light receiving surface 16 will flow out into the counter bore 54.

Incidentally, the constant temperature dry air 26 marked with an arrow in FIG. 4C shows that the air flows in a direction shown by the arrow. FIG. 4D three-dimensionally shows the sections of the second blast flow path 53, the through-hole 10, the counter bore 54 in the temperature transfer member of the third constant temperature controller 19. The arrow in FIG. 4B schematically shows a flow of the constant temperature dry air 26.

Embodiment 5

Figure 5:
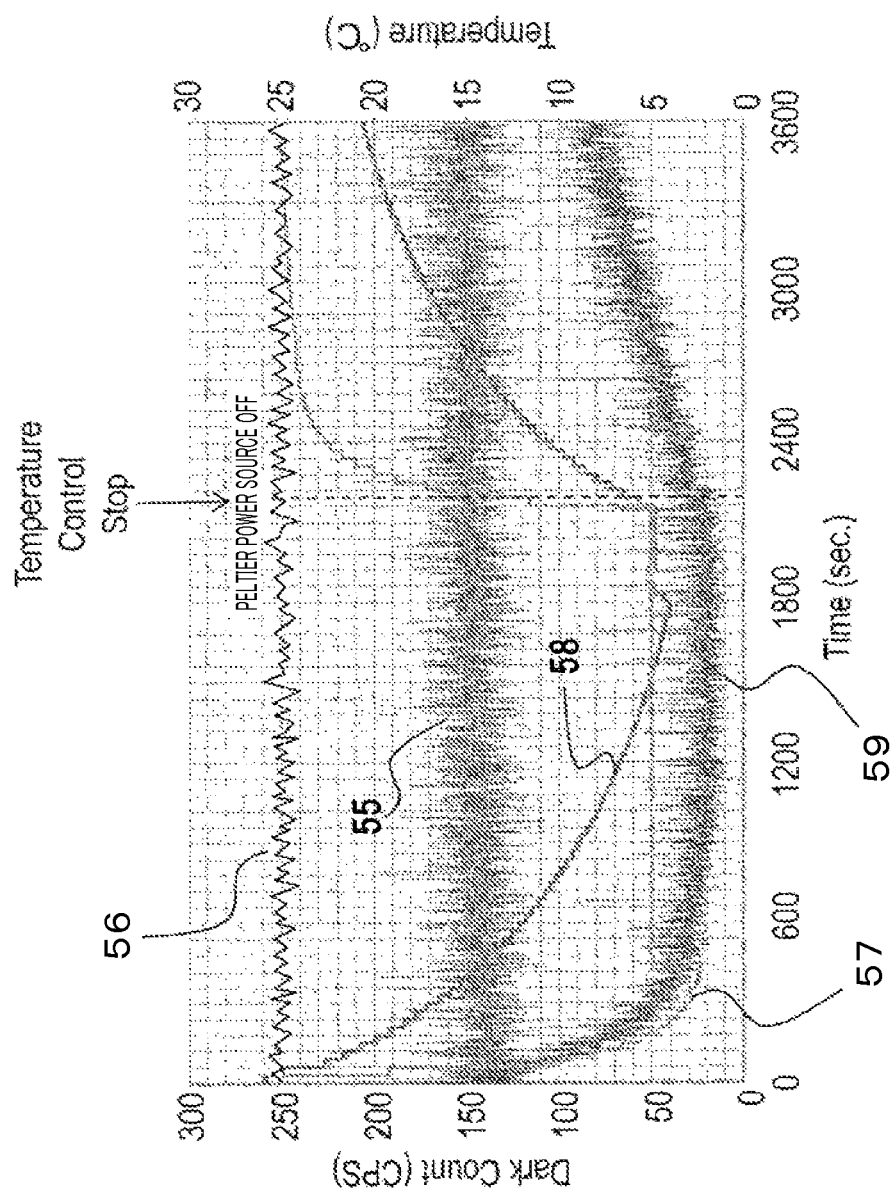
FIG. 5 is a diagram showing a time dependent change in temperature and a time dependent change in Number of Dark pulse counts (Nd) per second until reaching each set temperature according to an embodiment 5.

FIG. 5 is a diagram showing a temperature change until reaching each set temperature when the first constant temperature controller has been set to 25° C. and set temperatures of the second constant temperature controller and the third constant temperature controller have been set to 5° C. by using the weak luminescence measuring device of the present invention and a time-dependent change in number of dark pulse counts (Nd) per second, and respectively showing time-dependent changes in temperature 56 of the sample container, temperature 57 of the first plate member, temperature 58 of the light detector, Nd value 59 in a case where the constant temperature control concerned has been performed and typical value 55 of the Nd value in a case of no constant temperature control. The intra-device temperature was varying within a range from 22° C. to 25° C. The weak luminescence measuring device of the present invention may be also provided with a means for monitoring the temperature in the housing of the weak luminescence measuring device main body 1. The unit of the number of dark pulse counts (the Nb value) is COUNT PER SECOND (count number/second) and indicates an integrated value of the number of signal pulses in one second. Here, it is the one that the integrated value of the number of signal pulses per second has been continuously plotted from 0 to 3600 seconds. A result of temperature monitoring at that time is also superposed on the graph (a right axis).

In the present embodiment, the constant temperature dry air 26 was supplied through the second blast flow path 53 of the light detector 14 and the flow rate was 1 mL/min. In addition, quartz glass was interposed between the sample container 7 and the light detector 14. Since the thermal conductivity of quartz glass is low, it is easy to control the temperatures of the sample container 7 and the light receiving surface 16 independently and cooling of the sample container 7 can be avoided.

From FIG. 5, the temperature 57 of the first plate member 9 reached the set value of 5° C. after 500 seconds, the temperature 58 of the light detector reached the set value of 5° C. after 1800 seconds (after 30 minutes), the Nd value 59 when it had been controlled to the constant temperature of 5° C. in 1800-2160 seconds showed no fluctuation and the noise level was remarkably reduced more than the noise level of the Nd value 55 with no constant temperature control. Comparing the noise levels at 25° C. and 5° C. with each other in terms of Root Mean Square (RMS), it was 35.3 CPS for the Nd value 55 with no constant temperature control and was 12.6 CPS for the Nd value 59 when it had been controlled to the constant temperature. It is seen that after 2160 seconds have elapsed in FIG. 5, temperature control of the second constant temperature controller and the third constant temperature controller is released and as it returns to 25° C. that is the internal temperature of the weak luminescence measuring device 1, the Nd value is increased and the noise level is increased. In the present experiment, it can be confirmed from the number of dark pulse counts that the constant temperature dry air 26 is almost the same as the temperatures of the light detector 14 and the first plate member 9, and no dew condensation was generated on the light receiving surface 16 and the light receiving surface 16 in reality.

Figure 6:
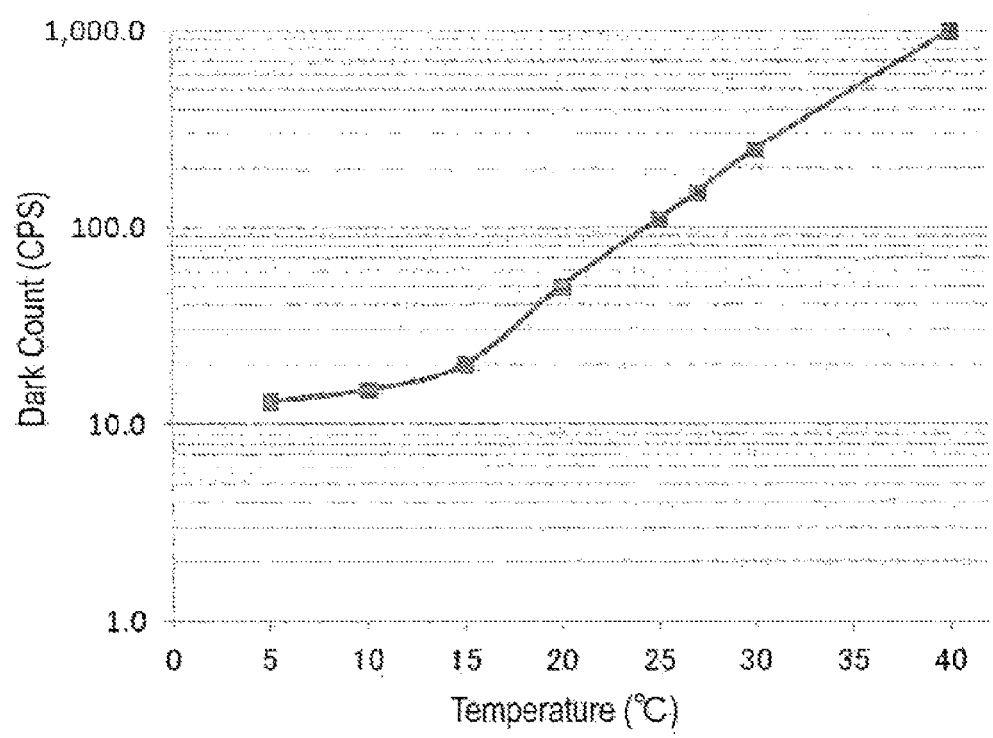
FIG. 6 is a diagram showing an average value of the Number of Dark pulse counts (Nd) per second depending on a difference in temperature according to the embodiment 5.

FIG. 6 is a diagram showing temperature dependence of an average value of the numbers of dark pulse counts (the Nd values) per second measured using the weak luminescence measuring device of the present invention. Although the light receiving surface 16 of the light detector 14 used in the present embodiment is the one that the incidence window has been configured by borosilicate glass and the photoelectric surface has been configured by bi-alkali (Sb—Rb—Cs, Sb—K—Cs), the average value of the dark count values became almost fixed at not more than 5° C. Needless to say, the incidence window may be made of quartz glass and UV cut glass, and the kinds of the photoelectric surface may be also the following ones, for example, Sb—Cs, multi-alkali (Sb—Na—K—Cs), (GaAs(Cs), InGaAs(Cs), InP/InGaAs(Cs), InP/InGaAsP(Cs), Ag—O—Cs and so forth.

Figure 7A:
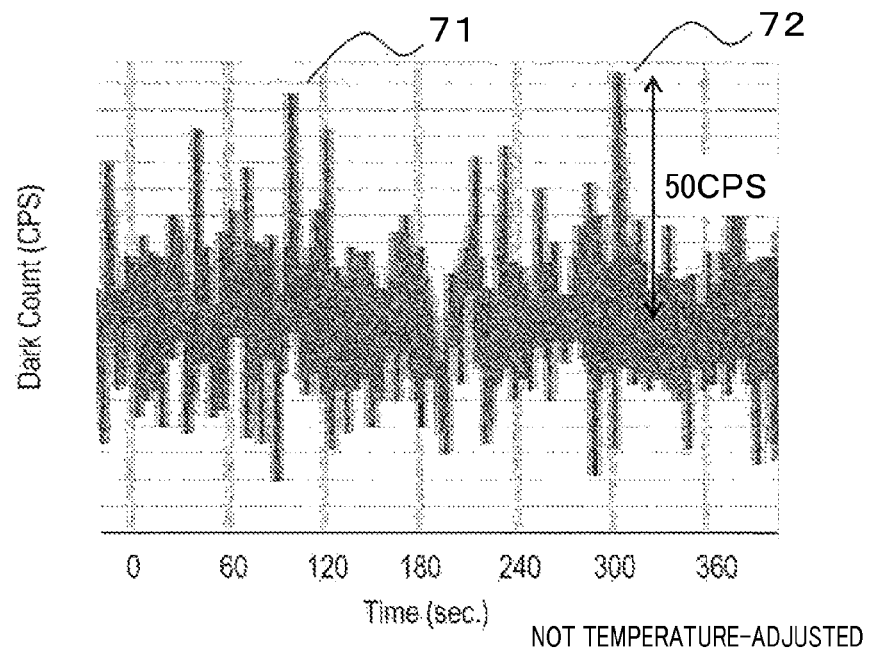
FIG. 7A is a diagram showing a result of measurement of weak pulsed light of 50 Count Per Second (CPS) in a case of not using temperature control by a constant temperature controller according to the embodiment 5.
Figure 7B:
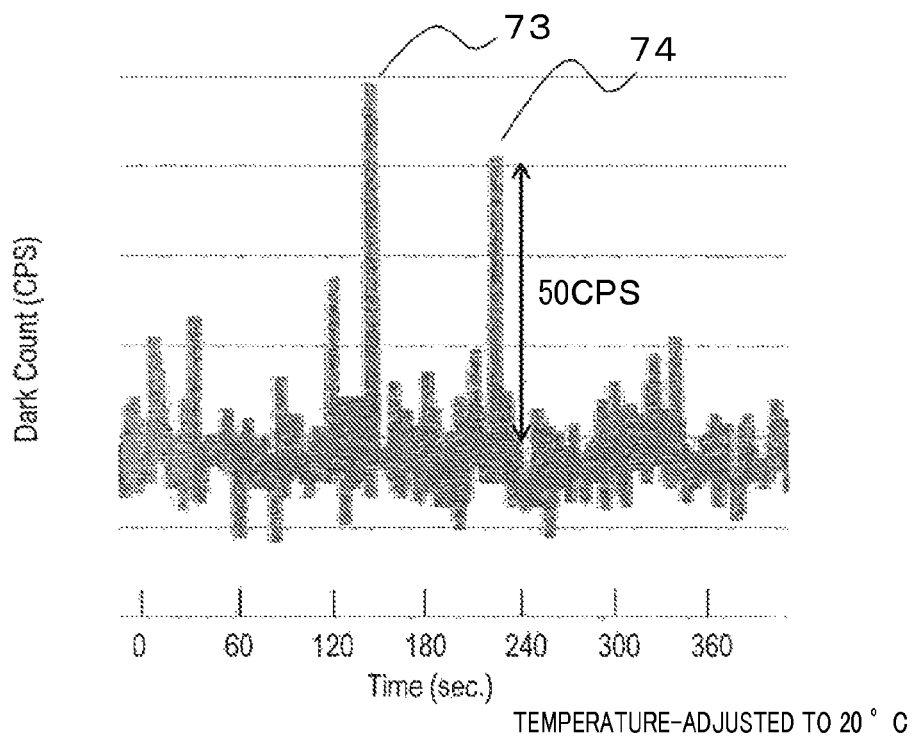
FIG. 7B is a diagram showing a result of measurement of the weak pulsed light of 50 Count Per Second (CPS) in a case where temperature control has been performed by the constant temperature controller according to the embodiment 5.

An example showing a result that a reduction in number of dark pulse counts (the Nd value) is effective to improve the detection sensitivity is shown in FIG. 7. FIG. 7 is a result of temperature dependence when a standard light source that emits extremely weak light has been shined in the form of pulses by using the weak luminescence measuring device of the present invention. With no temperature control in FIG. 7A, that is, at the time of 25° C. here, optical signals (71, 72) of 50 CPS are buried in noise and cannot be clearly observed. On the other hand, it is seen that at the constant temperature of 20° C., that is, simply by performing constant-temperature control of about −5° C. in comparison with the temperature when measured in FIG. 7A, it becomes possible to clearly distinguish optical signals (73, 74) from the light detector noise.

Figure 8:
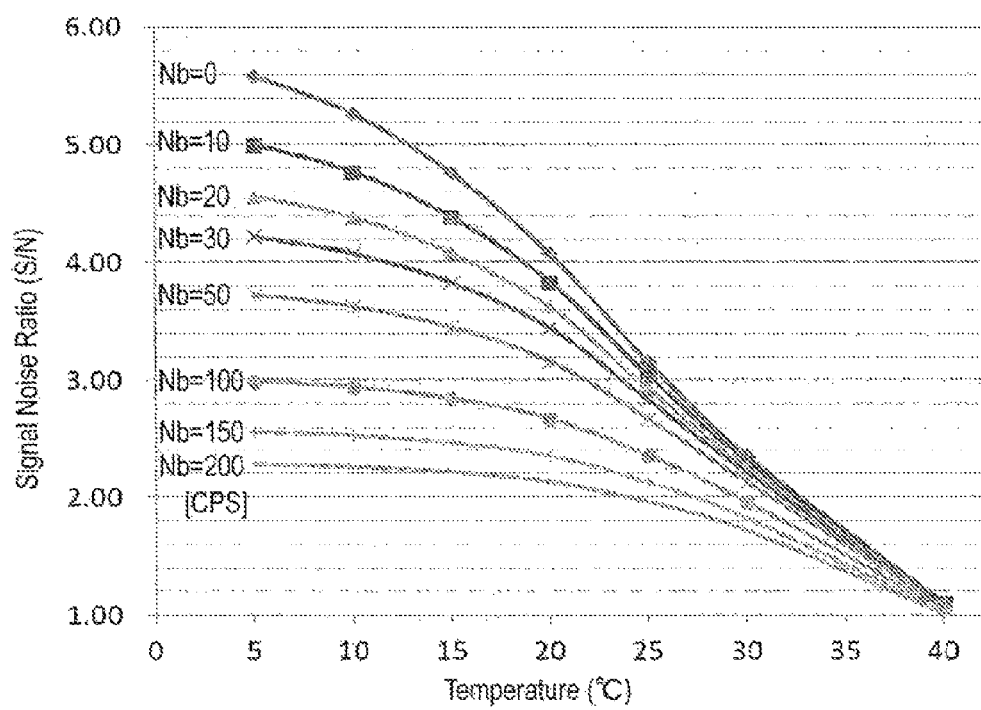
FIG. 8 is a diagram plotting a change in ratio of signal to noise (SN) ratio using differences in temperature and Nb value as conditions according to the embodiment 5.
Figure 9:
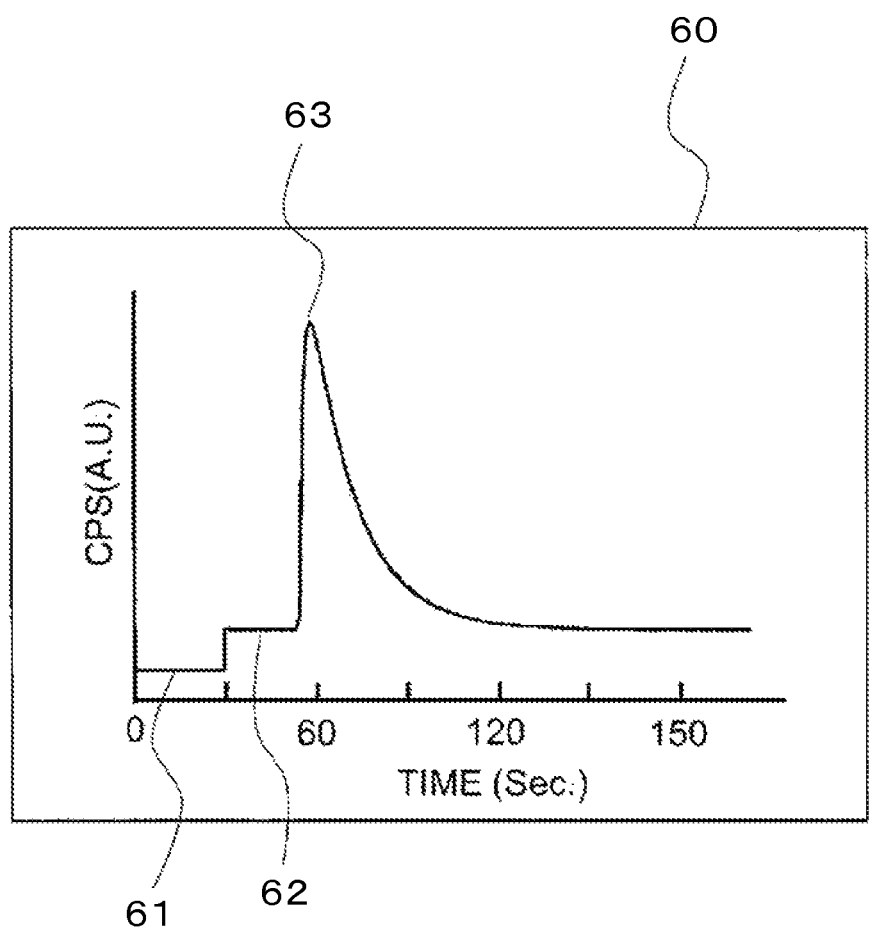
FIG. 9 is a diagram showing a typical example of ATP luminescence measurement data according to the embodiment 5.

FIG. 8 is a diagram showing a change in SN ratio relative to a difference in set temperature from a result that bioluminescence measurement of ATP has been performed with the temperatures of the first plate member 9, the light detector 14 and the light receiving surface 16 fixed, by using the weak luminescence measuring device of the present invention. The experiment was conducted in procedures as follows. The dispensing machine is introduced into the weak luminescence measuring device that has been introduced into the device, and first, the number of dark pulse counts is measured for 30 seconds in a state that an empty sample container is installed. Next, a luminescence reagent of ATP was dispensed into the empty sample container by the dispensing machine, a number of background optical signal pulse counts of the reagent was measured for 30 seconds, and thereafter a sample solution that contains ATP by 1 amol was dispensed into the sample container 7 and it was measured until the luminescent reaction was terminated. Data showing time-dependent changes in all of a number of dark pulse counts 61, a number of background light signal pulse counts 62, a number of luminescent signal pulse counts 63 is a time-dependent curve 60 of ATP luminescence that is the typical bioluminescence in FIG. 9. FIG. 8 is the one that a result of it performed by setting the first constant temperature controller 17 to 25° C., the second constant temperature controller 17, the third constant temperature controller 19 and the fourth constant temperature controller 24 to from 5° C. to 40° C. has been organized, and Formula (2) was used in organization. The SN ratio is expressed by the following formula on the basis of experiment data.

$$S/N = Ns/(Ns+2(Nb+Nd))^{1/2} \quad \text{Formula (2)}$$

Here, Nd is the number of dark pulse counts, Nb is the number of background light pulse counts of the reagent, the Ns value is a peak value (the number of luminescent signal pulse counts 63) of the number of ATP luminescent signal pulse counts.

First, ATP luminescence intensity was 50 CPS under any condition and was not changed. However, as shown in FIG. 8, since the number of dark pulse counts is changed in accordance with the set temperature, it is seen that the lower the temperature is, the more the SN ratio is improved. In addition, it is seen that as the Nb value is increased when the background light value Nb of the reagent undergoes a change of 0-200, the SN ratio is reduced. The background light of the reagent of the Nb value is different depending on the reagent and here as representative examples, examples of Nb=0, 10, 20, 30, 50, 100, 150, 200 were given. It was shown that the lower the temperatures of the light detector 14 and the light receiving surface 16 are, the more the SN ratio is improved in any case of the Nb value. In addition, it was shown that the lower the Nb value is, the more it becomes effective to lower the temperatures of the light detector and the light receiving surface.

REFERENCE SIGNS LIST

1 . . . weak luminescence measuring device main body, 2 . . . compressor, 3 . . . control device, 4 . . . open/close door, 5 . . . measuring room, 6 . . . control room, 7 . . . sample container, 8 . . . sample container holder, 8a . . . sample container holder, 9 . . . first plate member, 10 . . . through-hole, 11 . . . light transmission window, 12 . . . second plate member, 13 . . . first actuator, 14 . . . light detector, 15 . . . position control means, 16 . . . light receiving surface, 17 . . . first constant temperature controller, 18 . . . second constant temperature controller, 19 . . . third constant temperature controller, 20 . . . first constant temperature controller driver, 21 . . . second constant temperature controller driver, 22 . . . third constant temperature controller driver, 23 . . . constant temperature dry air blast nozzle, 24 . . . fourth constant temperature controller, 25 . . . fourth constant temperature control driver, 26 . . . constant temperature dry air, 27 . . . air dryer, 28 . . . first filter, 29 . . . second filter, 30 . . . heat insulation member, 31 . . . cooling surface of first electronic cooling element, 33 . . . radiating surface of first electronic cooling element, 34 . . . first heat discharger, 35 . . . first cooling medium introduction port, 36 . . . first cooling medium discharge port, 37 . . . cooling surface of second electronic cooling element, 38 . . . first metal block, 39 . . . radiating surface of second electronic cooling element, 40 . . . second heat discharger, 41 . . . second cooling medium introduction port, 42 . . . second cooling medium discharge port, 43 . . . second metal block, 44 . . . cooling surface of third electronic cooling element, 45 . . . radiating surface of third electronic cooling element, 46 . . . third heat discharger, 47 . . . third cooling medium introduction port, 48 . . . third cooling medium discharge port, 49 . . . circulation type pump, 50 . . . cooling medium storage tank, 51 . . . cooler, 52 . . . first blast flow path, 53 . . . second blast flow path, 54 . . . counter bore depression.

The invention claimed is:

1. A luminescence measuring device, comprising:
a holder that holds a container for containing a sample;
a plate member that holds the holder;
a light detector that detects luminescence in the sample, and has a light receiving surface facing a bottom surface of the container;
a first temperature control unit that performs control of a temperature of the light detector; and
a ventilator that sends air to the light receiving surface of the light detector,
wherein a first portion of the first temperature control unit is directly arranged on a first lateral side of the light detector, and a flow path is provided between a second lateral side of the light detector and a second portion of the first temperature control unit, and wherein the air is sent via the flow path, so that the air having the same temperature as that of the light detector is sent to the light receiving surface.

2. The luminescence measuring device according to claim 1,
further comprising a second temperature control unit that performs control of the temperature of the air such that the temperature of the air becomes the same as a temperature of the light detector.

3. The luminescence measuring device according to claim 1,
wherein the ventilator is provided with an air drying unit that dries air and sends air dried by the air drying unit to the light receiving surface.

4. The luminescence measuring device according to claim 1,
wherein the ventilator performs the air sending in parallel with the light receiving surface of the light detector.

5. The luminescence measuring device according to claim 1, further comprising:
a second temperature control unit that performs control of a temperature of the plate member,
wherein the plate member is provided with a flow path therein, and the ventilator performs the air sending via the flow path in the plate member whose temperature has been controlled by the second temperature control unit.

6. The luminescence measuring device according to claim 1, further comprising:
a second temperature control unit that performs control of the temperature of the light detector on a lateral side of the light detector,
wherein the second temperature control unit is provided with a flow path therein, and the ventilator performs the air sending via the flow path in the second temperature control unit.

7. The luminescence measuring device according to claim 3, further comprising:
a heat insulation member between the holder and the plate member.

8. The luminescence measuring device according to claim 1,
wherein a flow rate of the air to be sent from the ventilator is from 0.5 milliliters per minute to 3 milliliters per minute.

9. The luminescence measuring device according to claim 1,
wherein the plate member has a through-hole, and
the light receiving surface of the light detector faces the bottom surface of the container via the through-hole.

10. The luminescence measuring device according to claim 6,
wherein the through-hole can be opened/closed by a light shielding member and is in an opened state when measuring luminescence.

11. A luminescence measuring device, comprising:
a holder that holds a container for containing a sample;
a plate member that holds the holder;
a light detector that detects luminescence in the sample, and has a light receiving surface facing a bottom surface of the container;
a ventilator that sends air to the light receiving surface of the light detector; and
a plurality of temperature control units including a plate member temperature control unit that performs control of a temperature of the plate member;
wherein the plate member is provided with a flow path within the plate member,
wherein the second temperature control unit is directly arranged on a surface of the plate member that is exterior to the flow path of the plate member, and
wherein the air is sent via the flow path of the plate member and the temperature of the plate member is controlled by the second temperature control unit, so that the air having the same temperature as that of the plate member is sent to the light receiving surface.

12. The luminescence measuring device according to claim 11, further comprising:
a holder temperature control unit that performs control of a temperature of the holder,
wherein a controlled temperature by the second temperature control unit is lower than a controlled temperature by the third temperature control unit.

13. The luminescence measuring device according to claim 11,
wherein the ventilator is provided with an air drying unit that dries air and sends air dried by the air drying unit to the light receiving surface.

14. The luminescence measuring device according to claim 11,
wherein a flow rate of the air to be sent from the ventilator is from 0.5 milliliters per minute to 3 milliliters per minute.

15. The luminescence measuring device according to claim 11,
wherein the plate member has a through-hole, and
the light receiving surface of the light detector faces the bottom surface of the container via the through-hole.

* * * * *